US012593971B2

(12) United States Patent
Wang et al.

(10) Patent No.: US 12,593,971 B2
(45) Date of Patent: Apr. 7, 2026

(54) SYSTEMS FOR TRACKING DISEASE PROGRESSION IN A PATIENT

(71) Applicant: Iterative Scopes, Inc., Cambridge, MA (US)

(72) Inventors: Daniel Wang, Cambridge, MA (US); Jonathan Ng, Cambridge, MA (US)

(73) Assignee: Iterative Scopes, Inc., Cambridge, MA (US)

( * ) Notice: Subject to any disclaimer, the term of this patent is extended or adjusted under 35 U.S.C. 154(b) by 441 days.

(21) Appl. No.: 17/990,623

(22) Filed: Nov. 18, 2022

(65) Prior Publication Data

US 2023/0148855 A1 May 18, 2023

Related U.S. Application Data

(60) Provisional application No. 63/280,992, filed on Nov. 18, 2021.

(51) Int. Cl.
| | |
|---|---|
| *A61B 1/31* | (2006.01) |
| *A61B 1/00* | (2006.01) |
| *G06T 7/00* | (2017.01) |

(52) U.S. Cl.
CPC .......... *A61B 1/31* (2013.01); *A61B 1/000094* (2022.02); *G06T 7/0016* (2013.01); *A61B 1/000096* (2022.02); *G06T 2207/10068* (2013.01); *G06T 2207/20081* (2013.01); *G06T 2207/30032* (2013.01)

(58) Field of Classification Search
CPC ................ A61B 1/31; A61B 1/000094; A61B 1/000096; G06T 7/0016; G06T 2207/10068; G06T 2207/20081; G06T 2207/30032
See application file for complete search history.

(56) References Cited

U.S. PATENT DOCUMENTS

| | | | |
|---|---|---|---|
| 7,570,986 | B2 | 8/2009 | Huang et al. |
| 7,931,588 | B2 | 4/2011 | Sarvazyan et al. |
| | | (Continued) | |

FOREIGN PATENT DOCUMENTS

| | | |
|---|---|---|
| CA | 3055762 A1 | 10/2018 |
| CN | 104114077 A | 10/2014 |
| | (Continued) | |

OTHER PUBLICATIONS

Yao et al., "Motion-based camera localization system in colonoscopy videos," Medical Image Analysis, Oct. 2021, 73:102180, 21 pages.

*Primary Examiner* — Casey L Kretzer
(74) *Attorney, Agent, or Firm* — Fish & Richardson P.C.

(57) ABSTRACT

Systems and methods for tracking an evolution of a disease in a colon of a patient over time are configured for operations including receiving video data representing a colon of a patient; segmenting the video data into segments representing portions of a colon of the patient; extracting, from the video data based on the segmenting, a set of features representing locations in the colon of the patient; and registering the feature vector as representing the colon of the patient for tracking the evolution of the disease in the colon of the patient. The system can be configured to predict disease progression predict drug dosage for patients.

20 Claims, 10 Drawing Sheets

(56)     References Cited

U.S. PATENT DOCUMENTS

| | | | |
|---|---|---|---|
| 8,131,036 B2 * | 3/2012 | Collins | G06V 10/44 |
| | | | 382/128 |
| 2008/0117209 A1 | 5/2008 | Razeto | |
| 2009/0304248 A1 | 12/2009 | Zalis et al. | |
| 2010/0124365 A1 * | 5/2010 | Kanda | G06V 10/70 |
| | | | 382/128 |
| 2016/0106347 A1 * | 4/2016 | Patwardhan | G06T 7/0012 |
| | | | 600/407 |
| 2018/0263712 A1 | 9/2018 | Kitamura | |
| 2019/0286652 A1 * | 9/2019 | Habbecke | G06F 16/7837 |
| 2020/0364859 A1 | 11/2020 | Najarian et al. | |
| 2022/0028550 A1 | 1/2022 | Ng et al. | |
| 2023/0154580 A1 | 5/2023 | Wang et al. | |
| 2024/0112775 A1 | 4/2024 | Madan et al. | |
| 2025/0040901 A1 | 2/2025 | Averbuch | |

FOREIGN PATENT DOCUMENTS

| | | |
|---|---|---|
| CN | 111048170 A | 4/2020 |
| WO | WO 2008/093288 A2 | 8/2008 |

* cited by examiner

100

Processing Device
110

Memory
111

Instructions
112

Machine learning
module
113

Image processing
module
114

Prediction module
116

(Endoscope)
Video data
102

Electronic
medical
records (EMR)
data
104

Network
118

-Omics
data
106

Treatment
data
120

Registry
data
108

Data Sources, 103

500

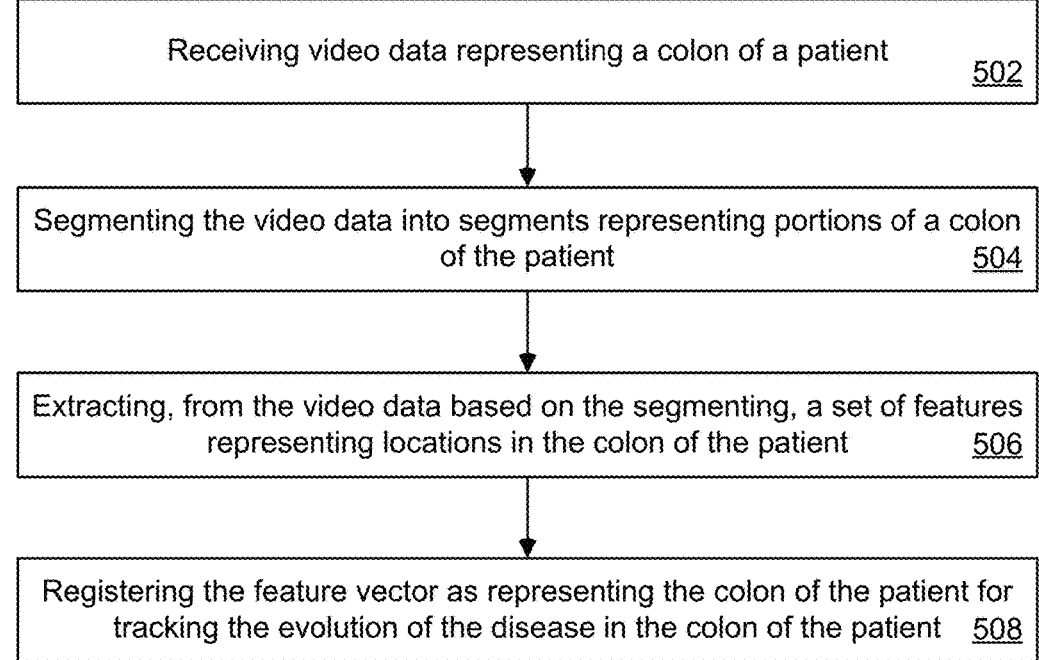

Receiving video data representing a colon of a patient          502

Segmenting the video data into segments representing portions of a colon of the patient          504

Extracting, from the video data based on the segmenting, a set of features representing locations in the colon of the patient          506

Registering the feature vector as representing the colon of the patient for tracking the evolution of the disease in the colon of the patient          508

FIG. 5

800

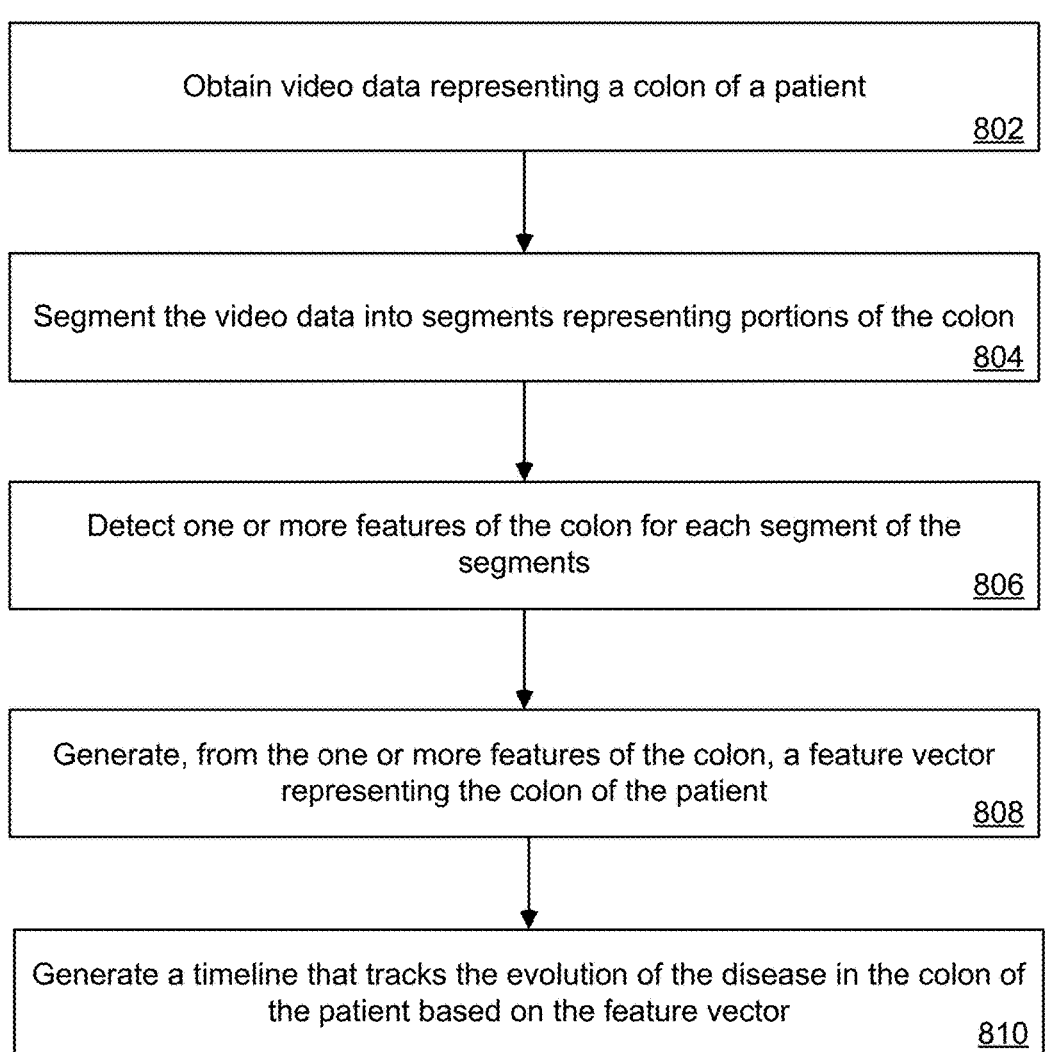

Obtain video data representing a colon of a patient

802

Segment the video data into segments representing portions of the colon

804

Detect one or more features of the colon for each segment of the segments

806

Generate, from the one or more features of the colon, a feature vector representing the colon of the patient

808

Generate a timeline that tracks the evolution of the disease in the colon of the patient based on the feature vector

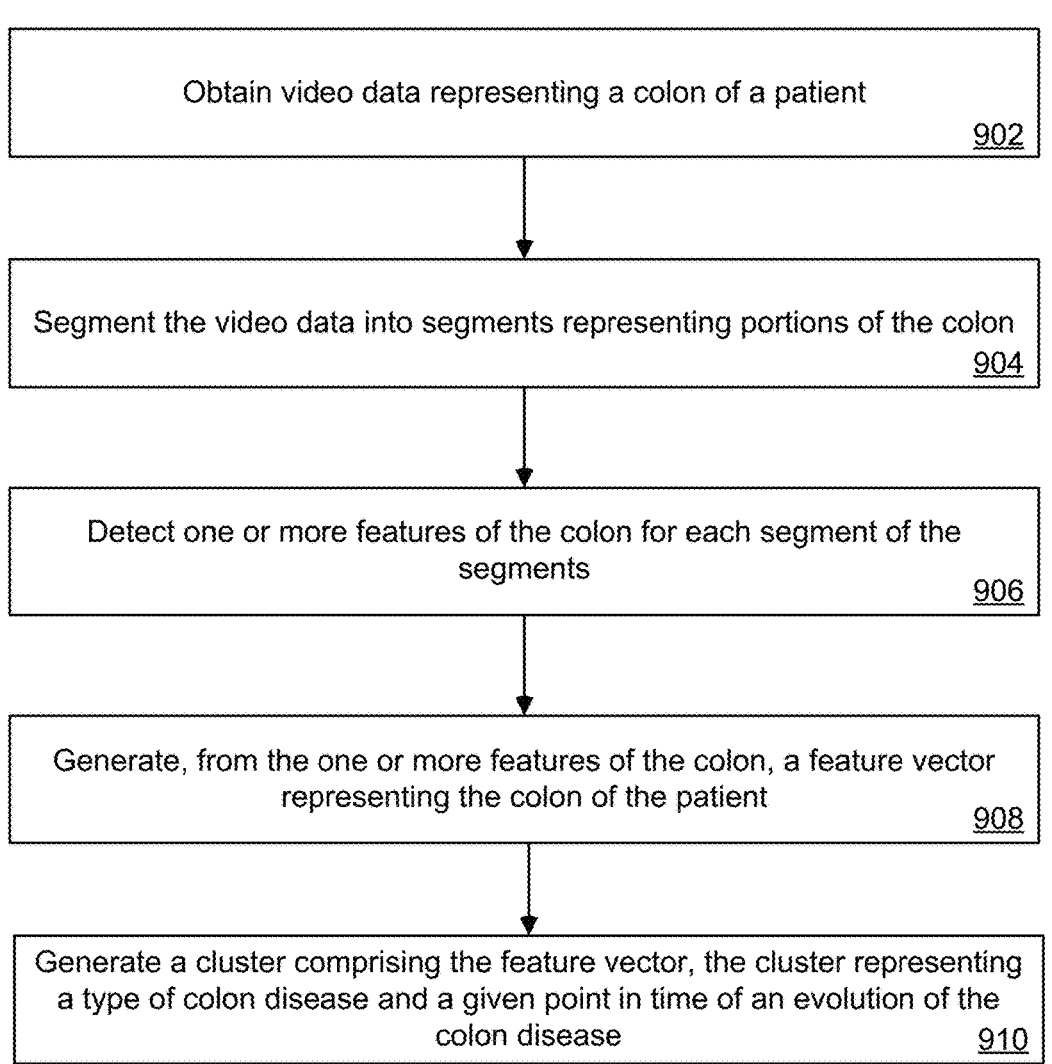

Obtain video data representing a colon of a patient

902

Segment the video data into segments representing portions of the colon

904

Detect one or more features of the colon for each segment of the segments

906

Generate, from the one or more features of the colon, a feature vector representing the colon of the patient

908

Generate a cluster comprising the feature vector, the cluster representing a type of colon disease and a given point in time of an evolution of the colon disease          910

FIG. 9

SYSTEMS FOR TRACKING DISEASE PROGRESSION IN A PATIENT

CLAIM OF PRIORITY

This application claims priority under 35 U.S.C. § 119(e) to U.S. patent application Ser. No. 63/280,992 filed on Nov. 18, 2021, the entire contents of which are hereby incorporated by reference.

TECHNICAL FIELD

This disclosure generally relates to systems and methods for tracking the evolution of diseases in the colon of a patient. Video data are aligned from a first endoscopy to a second endoscopy and tracked in videos from a first time to a second time.

BACKGROUND

An endoscopy refers to a nonsurgical procedure used to examine a patient's digestive tract. Typically, an endoscope, which is a flexible tube that includes a light and camera, is placed within a patient's digestive tract so that a doctor can view images (e.g., still images and/or video) of the patient's digestive tract. For example, during an upper endoscopy, an endoscope is passed through the mouth and throat into the esophagus of a patient, allowing a doctor to view the esophagus, stomach, and upper part of the small intestine. Similarly, an endoscope can be passed into the large intestine of a patient through the rectum to examine this area of the intestine (e.g., a colonoscopy). Endoscopic procedures allow physicians to evaluate several medical conditions, such as causes of stomach pain, appearances of ulcers, bleeding in the digestive tract, and detection of potential malignancies (e.g., polyps). Endoscopic procedures are a key endpoint for healthcare providers to measure IBD outcome and activity. The FDA also increasingly views endoscopic endpoints (as opposed to patient reported symptoms) as a key measure of drug efficacy and performance for IBD related clinical trials.

For assessment of colonoscopy videos, there is intra-rater and inter-rater subjectivity. There is a lack of objective measures for disease progression and response to therapy.

SUMMARY

This specification describes systems and methods for conducting longitudinal analysis of images or videos from endoscopic data retrieved from multiple endoscopies for patients in order to extract information and automatically determines changes within the patients' intestines. In some implementations, the system described will detect disease progression of colonic diseases in patients (e.g., Colorectal cancer, Ulcerative Colitis, Crohn's Disease, Diverticulum etc.).

There are a set of systems included for tracking disease progression in patients. A first system includes a data retrieval/data acquisition system that is configured to obtain endoscopy data (e.g., image, videos, metadata etc.) from multiple endoscopic procedures. The second system includes an image processing machine learning module that filters non-informative images or frames. The third system includes a feature identification and landmark detection machine learning module. This system is configured to determine details of various characteristics and features alongside the anatomical locations of these characteristics and features. This system writes this generated data database for access by the other systems. The fourth system includes a longitudinal analysis machine learning system that incorporates output data from the previously described systems to analyze changes in characteristics and features. The fifth system includes a machine learning system configured to automatically document and present the differences between endoscopic data of the same patient across time in a display unit or user interface. In some implementations, the machine learning system is able to interface directly with electronic health records. These systems can be combined to form a data processing system described herein.

The first system is configured to use a single or combination of machine learning models to extract data from the endoscopic processing unit and metadata from a patient. The data from the endoscopic processing unit may come in the form of images or videos. In some implementations, the data processing system is configured to directly interface with electronic health records (EHR) or electronic medical records (EMR) to retrieve any metadata that may be useful for all proceeding systems. In some implementations, only image and/or video data are needed for processing. In some implementations, both image and/or video data and metadata is required. In some implementations, all the data is required.

Metadata includes any EHR/EMR data that could be relevant, including previous surgeries performed on the patient involving the colon, clinical notes of practitioners relating to previously performed endoscopies, and medication that was prescribed in response to any colonic disease. For example, metadata regarding previous colectomies performed and which sections of the colon have been removed will be essential to this process. Metadata also includes the start and end time of the procedure that could be used to derive the duration of the procedure.

In some implementations, the retrieved image, video and/or metadata is processed in a cloud system to ensure data privacy. Depending on regulatory requirements or contract limitations, the image, video and/or metadata is subject to pre-processing (e.g., data masking), whereby any identifiable information (e.g., Name, Social Security Number etc.) tying the data back to a patient is removed and replaced with a non-identifiable code.

The second system includes an image processing machine learning module that serves two functions. The first function includes extracting information and determining whether an image or frame is informative. The second function includes removing uninformative frames (e.g., blurry frames, frames with bubbles, frames with shaky camera etc.). Depending on which machine learning module is used in the third system, a different filtering algorithm is implemented to filter out different types of frames.

In some implementations, the second system will analyze the metadata to determine what types of data may be useful in the longitudinal analysis conducted by the fourth system. This determination of useful metadata can be field/data type specific (e.g., incorporate date and time information) or be content based (e.g. machine learning algorithm conducts optical character recognition and determines if the content of the metadata might be relevant—this is especially important if the metadata is unstructured (clinical notes)).

Following from this implementation, the second system is able to detect, determine and filter out non-informative text (e.g., name of clinic previous endoscopy was performed at), while keeping all informative text as easily retrievable metadata by all the other systems specified in this patent.

For example, after performing an endoscopy, a clinician notes down key symptoms that were detected during the colonoscopy. Those notes or part of these notes may be detected as informative and stored in the system for further analysis (by the fourth system).

The third system consists of three separate modules. The first module detects and determines the features present (e.g., adenomatous polyps, ulceration, strictures). This first module is able to detects the presence of features within the intestines and determines the type of feature present. In some implementations, if the image or video data of the colonic procedure includes the excision of this feature (e.g., polypectomy to remove a polyp etc.), the second module is able to determine which of the detected polyps were removed. The second module determines the anatomical location of detected feature(s). Where relevant, the second module provides the anatomical location as an exact distance of detected features from the nearest landmark (e.g., adenomatous polyp C was 5 cm away from the splenic flexure etc.). The third module is configured to determine the type of colonic disease the detected feature based on image, video or metadata retrieved. In some implementations, the third module is able to generate a composite score which aims to capture disease progression of various colonic diseases (e.g., ulcerative colitis etc.). The modules in this system may be used independently or in conjunction with each other.

The fourth system is configured to incorporate data from all preceding systems to compare the changes in characteristics features at various anatomical locations in the small and large intestine over time. The fourth system is configured to analyze and determine the time frames of all incoming data (e.g., date) and arrange the data in a chronological order. Following which, the fourth system determines the differences between any detected features or characteristics. In some implementations, the fourth system is able to compare the disease progression of associated colonic diseases with the detected features by analyzing the changes in the symptoms representative of the colonic disease and/or the composite score.

For example, a patient was diagnosed with mild ulcerative colitis after a previous endoscopy was performed, with the inflammation ending prior to the splenic flexure (proctosigmoiditis). Through analysis of the images and/or video of the initial endoscopy, the fourth system is able to determine that inflammation ended 4 cm prior to the splenic flexure and had mild friability throughout the entire inflammation. However, in the follow-up endoscopy, the fourth system notes that the new inflammation now ends only 2 cm prior to the splenic flexure, which represents a slight increased severity in the progression of the disease. Moreover, there are now segments near the rectosigmoid junction that have signs of moderate disease (e.g., marked erythema). The fourth system is able to note the specific locations in which the disease has progressed in severity.

In some implementations, the fourth system described in this patent can predict areas of expected abnormality of significant clinical findings. In other words, the fourth system is able to detect changes in the features (e.g., polyps, ulcers etc.)/characteristics of the colon even in the absence of any features during follow-up endoscopies and recognize anatomical locations in the colon even if they are healthy.

For example, through incorporating information from clinical notes, the fourth system notes that a previous clinician of the patient had detected and excised an adenomatous polyp in the transverse colon, specifically 5 cm from the hepatic junction. During the next endoscopy, there were no polyps or complications (e.g., bleeding) detected at the same location. However, the fourth system is able to determine that the location of the previously performed polypectomy has healed.

In some implementations, the fourth system is able to determine a patient's response to medication/treatment that is prescribed by a previous clinician. The fourth system retrieves data of previous treatment options provided from the metadata retrieved in the first system. Following from the above example of a patient having been detected for Ulcerative Colitis in a prior endoscopy, the fourth system notes that this patient was prescribed topical 5-ASAs as part of the treatment plan by the previous physician. However, due to the increase in disease progression in the follow-up endoscopy, the fourth system notes that this specific medication of topical 5-ASAs and/or mode of delivery of this medication has proven ineffective.

The fifth system is configured to document and display the differences as analyzed in the preceding systems. In some implementations, the fifth stage is able to generate a report which displays these extracted and analyzed longitudinal differences between endoscopies. This report may include text, labeled or annotated images and/or videos. In some implementations, bounding boxes may be displayed in the labeled videos and/or annotated that specifically highlights the anatomical location where changes in the characteristics/features have been detected.

In some implementations, the fifth stage will include a user interface that allows for live displays of information to the GI. For example, before or during the follow-up endoscopy, the fifth stage may display labels or annotations informing the GI to pay closer attention to specific anatomical locations.

In some implementations, this system also includes the ability to export the relevant documentation of these changes into a data warehouse. This data can be retrieved at a later stage or combined with alternative data sources (e.g. information about detection of polyps) and could be transcribed into a patient's electronic health records/electronic medical records directly or could be stored elsewhere with some association with the related image/series of images or video.

The systems and methods described in this specification provide one or more of the following advantages for improving the continuity of care in patients.

The systems described facilitate tracking of disease presentation and severity over a period of time, ensuring continuity and follow-up of care for patients. Disease tracking is done through accurately tracking the progression of findings or features (e.g., polyps, ulcerations in Inflammatory Bowel Disease, stricturing of the colon etc.) that may be detected during the endoscopy. Oftentimes, in the healthcare system, patients are transferred to be under the care of different physicians resulting in disjointed or disrupted treatment plans. Patients may also be easily lost to follow-up if they migrate across state borders or countries. However, with the systems and methods described, physicians can always rely on our product to evaluate the appearance of the intestinal tract through endoscopy and determine the progression of the disease, if any.

For example, colon cancer, specifically familial adenomatous polyposis (FAP) is a genetic condition that presents itself as thousands of polyps in the colon that progresses over time. Currently, it is standard practice for GIs to track the progression of this disease as it directly influences the type of treatment prescribed to the patient, namely either resection of polyps as compared to performing a colectomy. However, due to the large number of polyps, it becomes difficult for physicians to determine the progression of the disease over time. The systems described in this specification would standardize the counting of polyps, thereby allowing an increasingly accurate diagnosis of the severity of the disease and its progression. In some implementations, a composite score is assigned that details the severity of the disease at a specific point in time (e.g., when the endoscopy is performed), allowing ease of comparisons over multiple endoscopies. This data-driven approach would assist physicians in determining the best course of treatment for a patient, and also allows for timely intervention The systems described facilitate evaluation of treatment outcomes to determine their efficacy and benefit to the patient by monitoring the healing process (e.g., after interventions such as endoscopic resection of polyps or surgical colectomies). The data processing systems enable visualization/detection of complications of procedures at an early point in time. Early detection of complications enables a medical service provider to address the complications in a timely fashion, ensuring the safety and well-being of the patient.

For example, after a patient with Crohn's Disease has a bowel resection, an ileocolic anastomosis is usually performed to join together the ileum and colon. Common complications that may arise include blood clots, scarring, stricturing, damage to surrounding structures, infections (which may lead to sepsis), anastomotic leakage amongst others symptoms. In some implementations, the physician will be informed prior or even during the endoscopy to pay closer attention to the anatomical location where the ileocolic anastomosis was performed and determine whether there are any complications present.

Embodiments of the system and processes that enable one or more of these advantages include at least the following.

In an aspect, a process for tracking an evolution of a disease in a colon of a patient over time includes the following actions. The process includes receiving video data representing a colon of a patient; segmenting the video data into segments representing portions of a colon of the patient; extracting, from the video data based on the segmenting, a set of features representing locations in the colon of the patient; and registering the feature vector as representing the colon of the patient for tracking the evolution of the disease in the colon of the patient.

The process includes generating a timeline representing the evolution of the disease in the patient, the timeline configured to associate each feature vector registered as representing the colon of the patient; and generating a plurality of feature vectors that are registered to the colon patient, each feature vector representing the colon of the patient at a different point in time on the timeline.

In some implementations, the process includes clustering the feature vector with one or more other feature vectors registered to respective other colons of other patients, wherein clustering comprises: comparing first values of the features of the feature vector to second values of the features of the one or more other feature vectors; and grouping the feature vector an another feature vector when the first values and the second values are within a threshold similarity.

In some implementations, the process includes obtaining non-video data comprising at least one of histology data for the patient, bio-markers data for the patient, and omics data of the patient; and extracting one or more additional features from the non-video data for adding to the feature vector.

In some implementations, the process includes generating a second feature vector for a second patient based on second video data representing the second patient; and registering the second feature vector as representing a colon of the second patient for tracking the evolution of the disease in the colon of the second patient, the second feature vector being stored in a registry with the first feature vector for a same time point in a timeline.

In some implementations, a feature in the set of features represents at least one of a detected ulceration, a detected erosion, a detected erythema, a detected reduced vascularization, tumors, polyps, a detected friability, or another disease marker.

In some implementations, a feature of the set of features is associated with additional data specifying one or more of a size of the feature, a density of feature in the colon, and an extent of the feature in the colon.

In some implementations, the operations further comprising performing dimensional grouping of features of the set of features based on at least one of: an anatomical section of the colon or segment of the video data; a frame sequence including the features; and a time value associated with one or more of the features.

In some implementations, the operations further comprising labeling the feature vector based on the features of the feature vector, the label specifying at least one of an ileum average size of erosion, an ileum extent of erosions, an ascending colon average ulceration size, an ascending colon erosion density, a transverse colon average ulceration size, a transverse colon erosion density, a descending colon average ulceration size, and a descending colon erosion density.

In some implementations, the video data represent a scope of a colon of the patient including at least one of a cecum, an ileum, and a rectum of the patient.

In some implementations, the operations further comprise: extracting a set of features from the video data based on a type of disease screening associated with the video data, wherein the set of features for the video are unique to the type of screening.

In some implementations, the type of disease screening comprises at least one of cancer detection, irritable bowel disease, ulcerative colitis, and Crohn's disease.

In some implementations, the operations include generating a cluster including the feature vector, wherein each cluster is associated with a particular set of variables that define a phenotype associated with that cluster.

In some implementations, the output data for the cluster comprise at least one of: a number of patients in the cluster for a specified time period; an average value for each variable in the cluster; or a range of values for each variable in the cluster.

In a general aspect, a method for tracking an evolution of a disease in a colon of a patient over time includes obtaining video data representing a colon of a patient; segmenting the video data into segments representing portions of the colon; detecting one or more features of the colon for each segment of the segments; generating, from the one or more features of the colon, a feature vector representing the colon of the patient; and generating a timeline that tracks the evolution of the disease in the colon of the patient based on the feature vector.

In some implementations, the timeline includes entries representing different points in time for the evolution of the disease for the patient, and wherein each entry of the timeline is based on a feature vector generated at the point in time for that entry.

In some implementations, the process includes predicting a disease progression of the disease at a future point in time based on one or more existing entries in the timeline.

In some implementations, the process includes predicting a disease progression of the disease at 52 weeks from an initial time based on a first feature vector representing the patient at the initial time and based on a second feature vector representing the patient at twelve weeks from the initial time.

In an aspect, a method for tracking an evolution of a disease in a colon of a patient over time includes obtaining video data representing a colon of a patient; segmenting the video data into segments representing portions of the colon; detecting one or more features of the colon for each segment of the segments; generating, from the one or more features of the colon, a feature vector representing the colon of the patient; and generating a cluster comprising the feature vector, the cluster representing a type of colon disease and a given point in time of an evolution of the colon disease.

In some implementations, the methods or processes described herein are performed by a data processing system comprising at least one processor and a memory storing instructions that, when executed by the at least one processor, perform the operations of the processes and methods described herein. In some implementations, the methods or processes described herein are stored as instructions in one or more non-transitory computer-readable media. The instructions, when executed by one or more processors, cause the one or more processors to perform the operations of the methods and processes described herein.

This disclosure incorporates, by reference in entirety, the contents of patent application Ser. No. 17/990,471, Titled "Anatomical Location Detection of Features of a Gastrointestinal Tract of a Patient," being filed on Nov. 18, 2022, concurrently with this disclosure.

The details of one or more embodiments of these systems and methods are set forth in the accompanying drawings and the description to be presented. Other features, objects, and advantages of these systems and methods are apparent from the description and drawings, and from the claims.

BRIEF DESCRIPTION OF THE DRAWINGS

FIG. 5 shows an example flow diagram for tracking an evolution of a disease in a colon of a patient.

FIGS. 8-9 show example processes for tracking disease progression in patients.

DETAILED DESCRIPTION

Figure 1:
FIG. 1 shows a data processing system for longitudinal alignment of colon videos over multiple time instances for tracking an evolution of a disease.

FIG. 1 shows an example of a data processing system 100 configured to execute one or more processes for an automated analysis of endoscopic and other health data for tracking an evolution of a disease in a colon of a patient over time. The data processing system includes a processing device 110, a memory 111 (or a computer readable hardware storage device) configured to host instructions 112, a machine learning system 113 configured to execute one or more trained machine learning platforms, an image processing module 114, and a prediction module 116.

The data processing system 100 is configured for using machine learning (e.g. of the machine learning module 113, described below) to determine measurements of various characteristics related to colon disease. The data processing system 100 is configured to obtain and incorporate data from various sources for training the machine learning system 113, performing scoring (e.g., by a scoring module) of endoscope video data 102. For example, the data processing system 100 includes electronic health records or electronic medical records (EMR) data 104 of patients in addition to video (endoscope) data 102 to use for scoring. The data processing system 100 also accesses -omics data 106 and registry data 108 for training the machine learning system 113 and performing scoring. In some implementations, functions of one or more of modules 113, 114, and/or 116 can be combined in part or in whole.

The data processing system 100 processes data from one or more of data sources 103. The data sources include video data 102, electronic medical records 104, -omics data 106, registry data 108, and treatment data 120. Each of these data sources 103 is subsequently described in further detail. These data sources 103 can be used individually or in any combination for tracking an evolution of a disease in a colon of a patient over time. For example, video data 102 alone may be sufficient to generate a confident score for a particular patient. In another example, video data 102 can be supplemented with EMR data 104, -omics data 106, etc. to increase confidence in a particular score or in an initial iteration of scoring.

The data processing system 100 is configured to obtain video data 102 from an endoscopic tower or endoscopic processing unit (not shown). The endoscopic tower includes an imaging device that is configured to capture image data or video data 102. In some implementations, the imaging device is an endoscope. An endoscope is an illuminated optical, thin, and tubular instrument (e.g., borescope) used to examine internal organs like the throat or esophagus. The endoscope can be shaped and configured to target specific organs, such as the bladder, kidney, bronchus, colon, and/or pelvis. In some implementations, the endoscope is flexible and includes a camera on one end. The camera can capture image data in the form of still images and/or video. The image or video data 102 can take the form of several data formats, such as RAW, JPEG, PNG, etc. In some implementations, the imaging device includes a digital camera that uses a charge-coupled device (CCD) and/or complementary metal oxide semiconductor (CMOS) to convert photons to electrons for digital processing.

The EMR data 104 includes records associated with individual patients. The EMR data 104 can include self-reported data of the patient. The EMR data 104 can include data obtained from physicians or other medical service providers from interacting with the patient. For example, the EMR data 104 can include a medical history for the patient, such as medical operations the patient has experienced, illnesses the patient has experienced, and physiological data associated with the patient.

The omics data 106 includes genetic or molecular profiles of humans. The omics data 106 includes genomes and the inter-relationships of particular genes. The omics data 106 can be used to provide context to other patient data, such as data acquired from patient registries 108 and/or from EMR data 104.

The registries data 108 includes a clinical data registry, all called a patient registry or disease registry. The registries data 108 includes a database that collects, organizes, and displays healthcare information, generally related to a particular disease and for a patient population. The registries data 108 can be structured such that trends across patient populations are identifiable. For example, the trends can indicate how patients have responded to various disease treatments. The trends can associate symptoms with scores that have been assigned to those symptoms and how the scores changed in response to particular treatments. The registries data 108 can be combined with the omics data 106 and the EMR data 104 to establish patient trends and track treatment outcomes.

The data processing system 100 is configured to use machine learning techniques to generate a patient score for colon disease and to predict disease progression for the patient. The machine learning techniques replicate how physicians interpret endoscope images. For example, the data processing system 100 determines which types of drugs are effective based on the level of activity of a disease seen in the images. The level of activity of the disease is based on a number of various sub-classifications represented in images or video obtained from the endoscope. These sub-classifications can include determining the presence of bleeding, inflammation, polyps, or similar symptoms that may occur from a colon disease. This process is subsequently described in greater detail with respect to the machine learning module 113, the image processing module 114, and the prediction module 116.

The data processing system 100 is configured to use machine learning techniques to perform landmark detection, described in further detail below. For example, machine learning models can be configured to extract features from the video data, the features representing particular locations in the GI tract. The video can be tagged with the locations at the points in time in which the feature(s) are present in the video. The data processing system 100 can store these tagged videos in the database to assist medical service providers to review patient data and to assist systems in automation of processing the video data. The machine learning models for landmark detection can be executed in parallel with the machine learning modules for scoring. In some implementations, the machine learning modules for landmark detection are executed in sequence with machine learning models that generate scores in a pipelined process.

The data processing system 100 is configured to automate various colon disease classification scores (i.e. Mayo Score, etc.), as previously indicated. The data processing system 100 ingests data from various sources, such as image or video data 102, EMR data 104, -omics data 106, and registry data 108. While data sources 102, 104, 106, and 108 are shown in FIG. 1, this list is not exhaustive. Patient data from other sources can also be incorporated into analysis for automation of scoring.

The data processing system 100 is configured to receive video or image data 102 from a procedure (e.g., from a colonoscopy). The image or video data 102 generally includes a sequence of frames, each representing a portion of the colon (or other such patient data). A subset of the frames or images of the video or image data 102 can represent symptoms of colon disease. The data processing system 100 is configured to identify the frames or images of the data 102 that represent symptoms and score the video including the frames accordingly.

The image processing module 114 is configured to process the image or video data 102 for identifying the presence of symptoms of colon disease. In some implementations, the image processing module 114 is a part of the machine learning module 113, wherein the image processing module extracts data from the images or videos, and the machine learning module 113 performs classification of the extracted data. For example, the image processing module 114 may perform thresholding operations or feature extraction based on signals received from the machine learning module 113 (e.g., setting threshold values or identifying features in the images to extract).

The image processing module 114 can process the images or frames of the video data 102 on an individual basis and/or in combination with one another to identify the presence of colon disease symptoms (e.g., bleeding, ulcers or sores, narrowing of the intestines, and so forth). For example, the image processing module 114 can process images frame by frame to identify a symptom presence in the frame (e.g., by signature matching a region of the image to a known signature representing a symptom). In some implementations, the image processing module 114 is configured to identify where in the image the symptom is manifested and identify, to other module (such as the machine learning module 113) which frames or sequence of frames are associated with a symptom.

The image processing module 114 generally is configured to draw bounding boxes or otherwise tag or identify images or frames as representing a symptom. However, how the image processing module 114 identifies the symptoms can be changed or updated based on feedback from the machine learning module 113. For example, the image processing module 114 can extract image data based on thresholds set or adjusted by the machine learning module 113. In some implementations, the machine learning module 113 is configured to update, based on training data, image signature data used for classification of the image or video data.

The image processing module 114 can process groups of frames or images of video data 102 together to identify a symptom. For example, if a symptom appears in single frame of the video, the identification of the symptom may be a false positive. The image processing module 114 can be configured to analyze the image in the context of a previous frame (or series of frames) or a subsequent frame (or series of frames). The image processing module 114 is configured to facilitate extraction and/or recognition, from image data, of features that inform generating of the classification score (e.g., by the machine learning module 113). For example, the image processing module 114 can facilitate detection of bleeding, polyp formation, etc. by applying one or more feature extraction processes using image processing. For example, these processes can include object detection, pixel thresholding, application of filters to the images or portions of the images, and so forth. In some implementations, the image processing module and the machine learning module 113 are combined into a single module, as machine learning techniques described herein are used for image processing (e.g., feature extraction, landmark detection, etc.).

The machine learning module 113 is configured to classify the data from the data sources 102, 104, 106, and 108 to determine a prediction of colon disease progression in the patient. For example, for video data 102, the machine learning module 113 is configured to regress colon disease classification scores from single frames or video clips to enable the prediction module 116 to generate a prediction of colon disease severity in the patient.

In some implementations, the machine learning module 113 includes a plurality of machine learning models. Each model of the plurality can be configured to process data from one of the data sources 103 (e.g., video data 102, EMR 104, omics data 106, and registry data 108) of data available to the data processing system 100. In some implementations, a single machine learning model is configured to receive data from two or more of data sources 103 and use those data in combination for generating a classification output. For example, a machine learning module 113 can receive image data 102 showing that inflammation is present in a patient's colon. In addition, the patient may have reported diarrhea symptoms, which can be captured in that patient's EMR data 104. These data together may suggest a stronger colon disease classification output. In some implementations, these data are processed by separate models, and the prediction module 116, further described below, combines this data into a prediction of colon disease progression in the patient.

In some implementations, the machine learning models are developed from data of different, unrelated diseases, such as colon disease and colorectal cancer. Generally, each set of training data is sourced from various clinical datasets, including those from pharmaceutical drug clinical trials, representing specific patients set or modalities. The data processing system 100 is configured to apply transfer learning between patients associated with different locations and different modalities from one another.

In an embodiment, the data processing system 100 performs an automated regression of various colon disease classification scores using the machine learning module 113. The machine learning module 113 obtains pre-existing videos and data from data sources 103. The machine learning module 113 annotates these data to derive an updated classification score for the image data 102. The machine learning module 113 receives data 103 from third parties such as hospitals and clinics. The data 103 received can be unstructured data that are transformed for use in the data model (e.g., in one or more machine learning models of the module 113). The data processing system 100 is configured to perform a multipronged approach to development of a machine learning model enhancing the generated predictions based on other features extracted from the data 103. The features extracted from this data can evolve as the models are trained. For example, the machine learning module 113 may be configured for segmenting ulcers at scale, identifying particular trends in the registries data 108, identifying symptoms from patient provided data in EMR records 104, and so forth. The machine learning module 113 passes the classification data to a prediction of disease progression as represented by the endoscopic data and the data from data sources 103

In some implementations, the data collected are from a given patient from a particular time point. Disease progression is tracked in a patient by observing patient symptoms for weeks, months or years. Different statuses of the patient are tracked, such as whether the patient is receiving drugs (e.g., yes or no), or what type of drug and what dosage is being received. Outcomes are correlated from one observation (e.g., set of measurement data of the patient a particular time) to another observation (e.g., a second set of measurement data of the same modalities at a second, later time). The disease progression is tracked for a specific symptom. For example, a specific portion of a patient's colon is tracked over time and associated with multiple sets of measurement data over that time.

Based on the analysis by the machine learning module 113, a prediction module 116 of the data processing system 100 is configured to generate a prediction based on the classification data output from the machine learning module 113. As subsequently described, the data processing system 100 receives data from a variety of sources 103, and ensures homogeneity amongst the data before the data is used for training of the machine learning model at module 113. The data processing system 100 is configured to perform data curation, which includes all the processes needed for principled and controlled data creation, maintenance, and management, together with the capacity to add value to data and data normalization that insure that a given data class with many sources such as video data from multiple clinical sites or EHR from various health system have compatible ensemble statistics. For example, video data are resampled to the same size and resolution and contrast and intensity normalized to have similar mean and standard deviation.

The data processing system 100 extracts the data from sources 103 and standardizes the data in a data repository (e.g., data store 201 subsequently described). The data processing system 100 is configured to segment the data based on time markers into three or more distinctive time frames. These time frames could be at weeks 0, 12 and 52, or they could be at other intervals. The data processing system 100 uses a combination of the data from the various time frames (in our example, weeks 0 and 12) to predict outcomes for week 52. In some implementations, the prediction can represent a patient disease progression for that time frame. In some implementations, the prediction can include additional recommendations such as treatment assignment and dosage suggestions. The prediction module 116 generates data that represents a prediction of how the detected symptoms in the patient (e.g., identified from the image data or other data sources) will progress in the future, and therefore recommend a treatment based on that disease progression. For example, if the disease with current treatment is predicted to become more severe in the future based on data presented, the prediction module may indicate as such and generate a recommendation that the dosage of the current drug be modified (increased), the addition of a new drug to assist in treatment or to switch the treatment altogether. However, other recommendations are possible. For example, outcomes where the disease with the current treatment is predicted to become neutral or improve, then smaller adjustment (changes in dosage) or no adjustments may be recommended.

Generally, based on the prediction of disease progression, the data processing system 100 is configured to recommend a drug therapy for the patient in the near or long term. The recommendation can be a change from a prior treatment recommendation. For example, the treatment recommendations include a specified drug regimen for a patient. The data processing system 100 correlates disease progression over time (e.g., week 0 and week 6) for a particular symptom, group of symptoms, or location in the patient. The data processing system 100 determines a rate or projected "slope" of disease progression based on each measurement set, the data processing system 100 is configured to extrapolate outcomes at distant time periods in the future (e.g., 52 weeks). The data processing system 100 can compare this projection to measured outcomes of other cohort patients and estimate whether a particular drug being observed is to be neutral, less effective, or more effective on a given patient. As previously stated, patient demographics are also included in the measurement sets and used to train the machine learning models for each disease.

The prediction module 116 generates a prediction output and associated treatment recommendation that is a combination of automated regression or classification and extracted features to represent a validated prediction. The predictions can include drug dosages and drug types for treatment of the patient. The data processing system 100 performs a multi-week or multi-month correlation of a state of the patient for each given symptom, rather than applying a single data point to the machine learning model. The data processing system 100 is thus configured to generate an increasingly complex prediction of disease progression based on endoscopic image data 102 in the context of both clinical and molecular data. The prediction represents a confidence in a particular clinical outcome if the status quo (e.g., maintaining current treatment level or no treatment) is maintained for future time period. The time period can be days, weeks, or months in the future (or a combination thereof). The prediction is generally paired with a recommendation of a treatment to achieve a more preferable outcome, such as curing symptoms or reducing colon disease severity, if applicable. The prediction ensures that treatment regimens that are currently being performed, if predicted to be ineffective, are changed. The prediction ensures that unnecessary treatments, such as application of medication that may be costly or have undesirable side effects, is minimized.

The prediction module 116 generally receives feature classification data from the machine learning module 113. However, the prediction module 116, and machine learning module 113 can be combined or can be separate modules executed by the processing device 110. In some implementations, the prediction module 116 is a portion of the machine learning module 113. In some implementations, the prediction module 116 receives input from the machine learning module 113 and uses the classifications of one or more machine learning models (e.g., for processing data from different sources 102, 104, 106, and 108) in a voting system to generate the score. In some implementations, the prediction module 116 uses a weighted average of classification values output from machine learning models of the machine learning module 113 or receive from another source. For example, the prediction module 116 may receive a strong classification from a polyp identification machine learning model, and receive data from EMR in which the patient reported bleeding. The prediction module 116 may combine these data to generate a prediction that colon disease in the patient is present. The prediction module 116 may generate a more accurate prediction of disease progression (e.g., that colon disease will become more severe in the short term) than would be generated from the machine learning model output in isolation. In some implementations, the prediction module 116 can receive conflicting classification outputs form machine learning modules or conflicting data from data sources 103. In this case, the prediction module 116 may generate prediction of slow/non-progression, despite a particular machine learning model outputting a classification output representing a strong indication that colon disease will increase in severity in the patient. Thus, the inclusion of data from many sources 103 results in a more robust severity score output than a score generated from a particular data source 102, 104, 106, or 108 in isolation. This severity score is then combined with other data sources 103 again to be used to predict disease progression and make treatment recommendations, as described herein.

The prediction from the prediction module 116 is presented to a user of the data processing system 100. The prediction can be presented as a value (e.g., a number), as a string (e.g., text), or in any similar format. In some implementations, the prediction is used to cause a data processing operation to occur based on the value of the prediction. For example, data from all or some or one of the data sources (103) or from the score generated across at least two different time periods is used to generate a prediction that the disease will increase in severity over a period of time (can be variable) above a particular threshold value, the data processing system 100 can be configured to generate an alert, alarm, generate a message, recommend immediate care, or perform some other operation. For example, if the prediction severity exceeds a threshold value, the data processing system 100 can be configured to alert a medical service provider or provide a particular visualization (which could include changing treatment type or dosage levels). If the score is below the threshold, the data processing system 100 can be configured to provide a different visualization. In some implementations, a patient record associated with the patient can be automatically updated to include prediction and treatment recommendation.

The computer-readable hardware storage device 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the memory 111 (e.g., computer-readable hardware storage device) includes code-segment (or other executable logic) having executable instructions.

The computer processors 110 can be communicatively coupled to a video capture device and configured to receive spatially arranged image data (e.g., video data) corresponding with one or more images captured by the imaging device. In some implementations, the computer processors 110 include a general purpose processor. In some implementations, the computer processors 110 include at least one applicable inference processor, accelerated processor which can be utilized in half, single, or double precision (16, 32, or 64 bit floating-point) calculation. The computer processor 110 can also include lots of compute unified device architecture (CUDA) cores, etc., or a combination of thereof. In some implementations, the computer processors 110 include a central processing unit (CPU). In some implementations, the computer processors 110 include at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code means such as the computer-executable instructions 112.

In some implementations, the network 118 enables a cloud-based or web-based system for processing the data. For example, the data processing system 100 can be operated as a web-based service over the network 118. In some implementations, the data sources 103 can be cloud-based and accessible remotely over network 118.

The data processing system can include a display unit (not shown) that is communicatively coupled to the computer processors 110 and configured to show results of the scoring and prediction processes described herein. The display unit can include an electronic display device. In some implementations, the display unit can be configured to act as a touchscreen display device. The display unit is configured to present a user interface. In some implementations, the user interface is a graphical user interface (GUI). The user interface is configured to allow a user of the data processing system 100 to interact with the data processing system 100 through graphical icons and visual indicators. The user interface can use a windows, icons, menus, pointer paradigm (WIMP) to allow a user to interact with the data processing system 100. In some implementations, the user interface 121 cooperates with the 120 to provide a user with a touchscreen GUI. Additionally, or alternatively, the user interface can include one or more input devices such as a mouse and/or keyboard communicatively coupled with the system 100. The user interface can also use a post-WIMP paradigm typically found in touchscreen-based GUIs. In some implementations, the user interface is configured to display images in the form of still photographs and/or videos.

In some implementations, the user interface includes a marker indicating a relative risk for the disease progression (e.g., severe, moderate, mild, none). For example, the data processing system 100 is configured to output a recommendation accompanied by a visual cue representing the disease progression prediction. In some implementations, the data processing system 100 is configured to mark "bad" data that was ineffective for assisting providing the recommendation, such as if the lens of a camera during an endoscopy was obscured. This may indicate to the user that more data are required (e.g., another observation or measurement set) for updating the disease progression prediction.

Figure 2A:
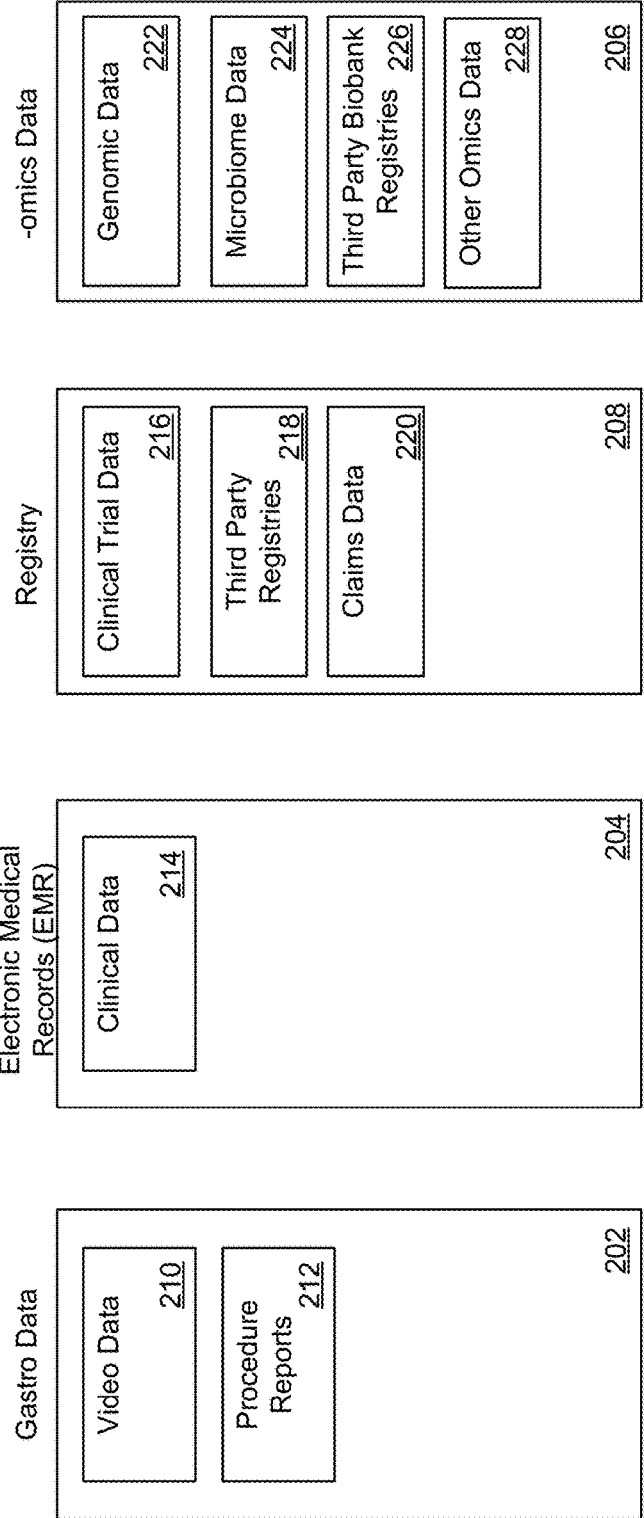
FIG. 2A shows example data sources for training and developing machine learning models for longitudinal alignment of colon videos over multiple time instances for tracking an evolution of a disease.

FIG. 2 shows example data sources 200 for training and developing machine learning models for detection of colon disease activity. Data sources 200 correspond to data sources 103 of FIG. 1. The data processing system 100 of FIG. 1 can be configured to communicate with a centralized colon disease data store 201. The centralized data store 201 is configured to communicate with each of the data sources including the gastro data 202, the EMR data 204 (e.g., similar to EMR data 104), the registry data 208 (e.g., similar to registry data 108), and the -omics data 206 (e.g., similar to -omics data 106 of FIG. 1). Generally, the centralized data store 201 can store data from multiple individual data sources 202, 204, 206, and 208 in a common structured system. For example, the data sources 202, 204, 206, and 208 can be 3rd party data sources or segmented data stores confined to particular data formats, particular data structures, and/or particular data accessible by particular systems. The centralized data store 201 retrieves data from the sources 202, 204, 206, and 208 can combine the data in to facilitate processing by the machine learning module 113, prediction module 116, and so forth for the data processing system 100.

As previously described, the data processing system 100 is configured to store these data or portions thereof in a data store 201 for analysis. Data store 201 represents an interface for accessing the data from various sources 103. The actual data need not be stored in a centralized database. For example, various data of sources 103 that are collected for analysis reside in various systems and generally include a superset of information is useful for analysis an aggregation. The data 202, 204, 206, or 208, or a portion thereof, can be included in a relational database. The data 202, 204, 206, or 208, or a portion thereof, can be part of a specific EMR or HER system and can be ingested and stored in cloud buckets. These data can be searched directly from the files stored using data connectors. Other data such as omics data, such as omics data 206, are too large to be incorporated in traditional databases but derivatives of these data can be generated such as gene variants, gene expression and pathway analysis or aggregates that represent specific subpopulation can be generated and are useful to describe behavior a particular subset of patients.

As previously described, the data processing system 100 is configured to ensure homogeneity amongst the data before the data is used for training of the neural network(s), such as through data curation. In an example, the data processing system 100 curates EHR and EMR data 204 entails adding timestamps across all datasets. Missing variables can be assigned by applying a Bayesian regression and standard statistics for feature selection can be used to determine the continuous baseline variables for significant differences between the one-year endoscopic remission and active groups.

The gastro data 202 generally includes data related to endoscopic procedures. For example, the gastro data 202 can include video data 210 (e.g., similar to the video data 102 previously described). The gastro data 202 can also include other data associated with the endoscopic procedure used to acquire the video data 210. For example, the gastro data 202 can include procedure reports 212 that include data about the patient when the procedure was performed, how the procedure was performed and what the video data represents (e.g., a particular region of the intestines or other portion of the body). The procedure reports 212 can include any data provided by the patient or the medical service provider that is related to the procedure.

The EMR data 204 include medical records for particular patients (similar to EMR data 104 previously described). The EMR data 204 can include data that conform to standard forms. The EMR data 204 can include clinical data for a patient that is provided by a medical service provider in response to a patient visit or telehealth interaction. Generally, the EMR data 204 are on a per-patient basis. This provides a rich history for a particular patient, and the patient's EMR data 204 can be imported to the centralized colon disease data store 201 when the patient data is being processed by the data processing system 100.

The gastro data 202 includes features that are used for classifiers for the machine learning models subsequently described. The values of the feature data affect how the scoring is performed by the machine learning model. For example, an endoscopy classifier receives feature data describing the patient as received from endoscopy procedures of the patient. These features can be represented in the video data 102. The values of the features affect how the machine learning model classifies the prediction for disease progression in the patient. The gastro data 202 features can include values that represent, for an endoscopy classifier, one or more of the following. The gastro data 202 features can include values that represent a location of the endoscopy, such as a lower GI endoscopy. The gastro data 202 features can include values that represent a presence of ulcers and/or a number of ulcers. The gastro data 202 features can include values that represent a relative vascularity, such as a percentage decrease of vascularity. The gastro data 202 features can include values that represent presence of erosions, and a number of the erosions. The gastro data 202 features can include values that represent presence or absence of bleeding in the GI tract, and a number of times bleeding was observed (e.g., a number of frames including evidence of bleeding). The gastro data 202 features can include values that represent erythema in GI tract). The gastro data 202 features can include values that represent a friability (e.g., in GI tract). The gastro data 202 features can include values that represent a size of ulcers or erosions. The gastro data 202 features can include values that represent a presence of stenosis (e.g., narrowings) of the GI tract. The gastro data 202 features can include values that are associated with an upper GI endoscopy (e.g., that specified as located in the upper GI endoscope data). The gastro data 202 features can include values that represent a total ulcerated surface (e.g., presence or absence of this surface, and a percentage of the tract including such a surface). The gastro data 202 features can include values that represent a surface affected by disease (e.g., as a percentage of the total surface). The gastro data 202 features can include values that represent a disease location in GI tract. The gastro data 202 features can include values that represent a number of lesions observed (e.g., at the case level). The gastro data 202 features can include values that represent a presence of cobblestoning in the tract. The gastro data 202 features can include values that represent a presence of deep ulcers. The gastro data 202 features can include values that represent a type of Crohn's disease observed (e.g., non-stricturing, non-penetrating, stricturing, penetrating, stricturing and penetrating, or perianal). The gastro data 202 features can include values that represent a presence of dysplasia in the patient. The gastro data 202 features can include values that represent whether activity at a biopsy site is proximal or distal.

The EMR data 204 includes data representing features that are used for classifiers for the machine learning models subsequently described. For example, a concomitant medications classifier contributes value to the prediction of disease progression based on whether these medications are being used by the patient. The data can include whether the patient is using diphenoxylate or opiates as anti-diarrheal medication. The values of the feature data affect how the scoring is performed by the machine learning model. In another example, a demographic classifier receives feature data including demographics data about the patient, which can affect how scoring is performed. For example, the demographics features can include age, sex, reproductive history, smoking status, and race or ethnicity. In another example, a physical examination classifier receives feature data including patient data obtained from physically examining the patient by a physician. For example, the features for this classifier can include data from a patient medical history which may indicate ileocolonic resection. The feature data can include data indicative of one or more of the presence or absence of an anal fissure, a fistula or abscess, and the presence or absence of one or more complications such as uveitis, pyoderma gangernosum, erythema nodosum, and/or arthralgia. The feature data can include data from physicians' global assessment of the patient (e.g., indicating the presence or absence of a condition). The EMR data 204 features can include values from pathology laboratory results, such as representing serological profiling results for a time period. The feature data include data values representing a history of medications prescribed to the patient, including current medications and biologics. The EMR data 204 features can include values that represent whether the patient has used biologics. The EMR data 204 features can include values that represent disease activity (e.g., whether a disease is active or inactive). The EMR data 204 features can include values that represent a colon disease type, such as whether the type includes UC or CD. The EMR data 204 features can include values that represent a disease duration (e.g., in years). The EMR data 204 features can include values that represent a history of surgery for the patient (e.g., whether it has occurred, what surgery has occurred, and when surgery has occurred). The EMR data 204 features can include values that represent whether steroid-free remission has occurred. The EMR data

204 features can include values that represent fistula drainage (e.g., an extent or occurrence). The EMR data 204 features can include values that represent whether the patient has experienced pain or activity restriction (e.g., frequency and severity values associated with either or both). The EMR data 204 features can include values that represent a degree of induration for the patient. The EMR data 204 features can include values that represent a presence or size of an abdominal mass in the patient. The EMR data 204 features can include values that represent whether sexual activity has been restricted. The EMR data 204 features can include values that represent a history of flaring (e.g., during a study associated with the patient). The EMR data 204 features can include values that represent a hospitalization history for the patient (e.g., time, duration, frequency, etc.). The EMR data 204 features can include values that represent a history of thrombosis for the patient (e.g., frequency, location, and/or severity).

In another example, the EMR data 204 features can be associated with an environmental classifier. The features can include results from the short colon disease questionnaire (e.g., an SIBDQ). The features can include values representing a patient diet, such as whether dairy has been consumed. The features can include values representing environmental exposures of the patient, including whether over the counter (OTC) drugs have been consumed by the patient, patient infections (e.g., types, locations, frequencies, etc.), and whether the patient has traveled or undergone major life events that may contribute stress to the patient's life. The features can include values representing relevant family history of disease. The features can include values representing fecal incontinence in the patient in the past. In these examples, values for these features can affect the weightings of a neural network (or other machine learning model) used for generating predictions of disease progression, as subsequently described.

The registry 208 includes patient data across patient populations. The registries can include anonymized health data that relates health trends to particular symptoms, colon disease scores, patient phenotypes, and so forth. The registry data 208 can include data representing results for how different treatments for different stages of a disease affected patients.

The registry data 208 includes clinical trial data 216. The clinical trial data include results and other data from studies, experiments, and clinical trials that test treatment regimens. The treatment regimens can include drug therapy, physical therapy, surgery, or other possible treatments.

The registry data 208 include third party registries 218. The registries 218 can be existing or established databases accessible by subscription or for free. These registries provide large amounts of data for a treatment space that can help inform the machine learning module 113, and/or prediction module 116 as to how to score symptoms and to predict how colon disease may progress in a patient with particular symptoms or associated with a particular patient history.

The registry data 208 includes claims data 220. The claims data 220 includes billing codes or other standardized data that physicians, pharmacies, hospitals, and other medical service providers submit to payers (e.g., insurance companies, Medicare). Claims data 220 generally includes a standard format across a wide variety of systems. The codes associated with services performed are a standard set of pre-established codes that describe specific diagnoses, procedures, and drugs. Additionally, nearly every encounter that a patient has with the medical system leads to the generation of a claim, creating an abundant and standardized source of patient information. The claims data 208 can be used to determine how patients are generally interacting with healthcare, both at an individual level and across patient populations.

The -omics data 206 includes genetic or molecular profiles of patient populations. The omics data 206 can provide a context as to how a given patient responds to a given treatment. Patients may be grouped by common expressions shown in omics data 206, and the machine learning module 113 and prediction module 116 can generate predictions based on correlations found in the data. Generally, the omics data 206 include genomics, which include a patient genome or genomic data 222. The omics data 206 include proteomics data representing sets of proteins produced by an organism. The omics data 206 include transcriptomics data such as sets of RNA molecules, including mRNA, rRNA, tRNA, and other non-coding RNAs relevant to treatment outcomes. The omics data 206 include pharmacogenomics data representing an effect of variations within the human genome on response to drugs. The omics data represent phenotypic traits, such as comprehensive description of disease symptoms in a patient. Additionally, the omics data 206 can include microbiome data 224 and third party biobank registries 226 including any of the foregoing data. Other omics data 228 can also be included.

In some implementations, the omics data 206 includes data representing features that are used for classifiers for the machine learning models subsequently described. For example, a genomic classifier can be applied to the omics data 206. The -omics data 206 can include feature data having values representing genome sequencing from blood for analysis by the molecular genomics classifier. Other feature data for the molecular genomics classifier can include bisulfite sequencing (RRBS) data from blood of the patient. The -omics data 206 can include feature data having values representing ChIP-sequencing for the patient and/or other patients. The -omics data 206 can include feature data having values representing HLA-DR genotyping for the patient and/or other patients. The -omics data 206 can include feature data having values representing genome sequencing from saliva of the patient.

In another example, a molecular microbiome classifier can be applied to the omics data 206. The -omics data 206 can include feature data having values representing a 16s microbiome sequence from stool of the patient and/or a 16s microbiome sequence from a biopsy of the patient. In some implementations, the -omics data 206 can include feature data having values representing metagenomics, metatranscriptomic information, metabolite profiling results for the patient, and/or virome data associated with the patient.

In another example, a molecular classifier can be applied to the omics data 206. The -omics data 206 can include feature data having values representing epithelial cell profiling from biopsy of the patient and/or single cell assay from a biopsy of the patient.

In another example, a transcriptomics classifier can be applied to the omics data 206. The -omics data 206 can include feature data having values representing a transcriptome sequence from a biopsy of the patient and/or a single-cell RNA sequence from a biopsy of the patient. In some implementations, the data can include proteomics data (e.g., proteomic sequencing) as feature data. In these examples, values for these features can affect the weightings of a neural network (or other machine learning model) used for generating predictions, as subsequently described.

In another example, a laboratory results classifier can be applied to laboratory results from the patient. The results can be included in the -omics data, registry data 208, and/or EMR data 204. The laboratory results data can include feature data having values representing an activity of a blood sample of the patient. The laboratory results data can include feature data having values representing fecal calprotectin or lactoferrin of the patient. The laboratory results data can include feature data having values representing Haematocrit levels for the patient, either at a point in time or over a period of time. The laboratory results data can include feature data having values representing serum CRP/C-reactive protein levels in the patient. The laboratory results data can include feature data having values representing Pharmacokinetics (PK) data associated with a patient (such as in response to a drug therapy). The laboratory results data can include feature data having values representing histology results for the patient. The laboratory results data can include feature data having values representing a full blood analysis of the patient, including values for white blood cell counts (WBC), hemoglobin (HgB), platelets, albumin, creatinine, and/or ESR levels. The laboratory results data can include feature data having values representing a urea analysis of the patient. The laboratory results data can include feature data having values representing liver function tests of the patient. The laboratory results data can include feature data having values representing ferritin, B12, Folate and VitD levels in the patient. The laboratory results data can include feature data having values representing SCFA levels in stool of the patient. The laboratory results data can include feature data having values representing basal metabolite panel in the patient. The laboratory results data can include feature data having values representing one or more tests, such as a fecal lactoferrin test and/or a fecal occult blood test (FOBT). The laboratory results data can include feature data having values representing blood tests to identify perinuclear anti-neutrophil cytoplasmic antibodies (pANCA), anti-*Saccharomyces cerevisiae* antibodies (ASCA), anti_CBir1_antibodies, and/or anti_OmpC_antibodies. In these examples, values for these features can affect the weightings of a neural network (or other machine learning model) used for generating predictions, as subsequently described.

In another example, a symptoms classifier can be applied to symptoms data from the patient. The results can be included in the -omics data, registry data 208, and/or EMR data 204. The symptoms data can include feature data having values representing a number of liquid stool per week for a patient, a bowel frequency for the patient, data representing rectal bleeding in the patient (e.g., frequency and severity), a general well-being of the patient (e.g., from survey data), abdominal pain during a week as reported by the patient, an urgency of defecation reported by the patient, and so forth.

Generally, the gastro data 202, the EMR data 204, the registry data 208, and the omics data 206 are stored as structured data in the centralized colon disease data store 201. Features can be extracted from any of the data stored in the data store 201 for use during classification by the machine learning module 113, scoring by a scoring module, or generating predictions from the predictions module 116.

Another source of data can include biomarkers data. Biomarkers can include data from one or more of the previously described data sources. Generally, biomarkers include any measurable indicator of a severity or presence of colon disease. Generally, the indicator may be chemical, physical, or biological, and the measurement may be functional, physiological, biochemical, cellular, or molecular. Examples of biomarkers include, in addition to data previously described, physiological data such as blood pressure, heart rate, etc. In some implementations, biomarkers include molecular indicators such as carcinoembryonic antigen (CEA) or other blood based biomarkers.

The data from each of sources 202, 204, 206, and 208 are normalized and/or standardized before being stored in the centralized data store 201 (also called the real-world data (RWD) data store). To standardize data, actions are taken to ensure that all fields or values that are used in the machine learning models are populated. If data are missing, the fields can be populated with default values or null values (e.g., those values are discarded in the models). In some implementations, a request is automatically generated to flag missing data to a relevant user. For example, an alert can be generated and sent (e.g., via email) to a patient or physician to complete a form.

For each set of data, specific operations can be performed to normalize and/or standardize that data. For example, video data can be converted to a particular format that is compatible as an input for the machine learning models. The video data can be preprocessed so that frames including bad data (e.g., blocked or dark frames) are removed. Video data can be reduced to a standard length or number of frames. Statistical analyses can be performed to ensure that the video data satisfies one or more data quality metrics, such as comparing the video to color/hue averages of other videos of the video library, etc. In some implementations, forms (such as EMR or EHR) can be checked to ensure all fields are populated before machine learning model analysis is performed. In some implementations, the data processing system ensures that all data received from a particular source has the same units (e.g., size in centimeters or inches, etc.).

Data normalization includes ensuring that data being received by the machine learning model is within expected ranges of values. For example, if demographic data suggests a patient is too young (e.g., negative years old) or too old (e.g., hundreds of years old), a data quality flag can be raised to request correction of the data. This example is illustrative, and other similar checks can be performed. For example, if data received in the timeline are too far apart for correlation between multiple machine learning model outputs for the timeline, the data processing system 100 can indicate that additional data are needed. More specifically, if the time period between two observations or measurements of patient data is too long, the data processing system can indicate a lower likelihood of correlation or confidence or request additional data.

Figure 2B:
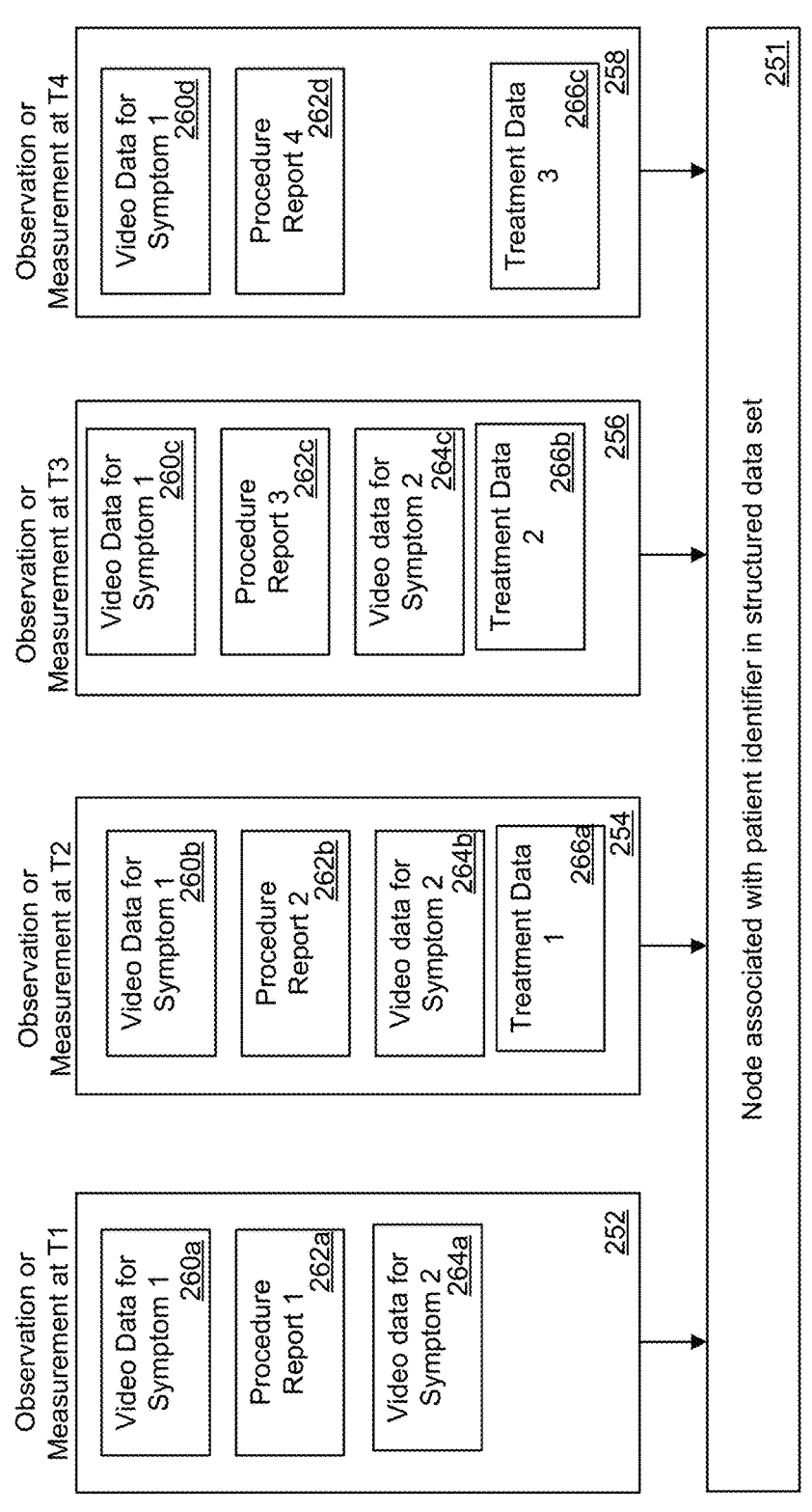
FIG. 2B shows a record of real world data (RWD) for a patient for a timeline at a node storing a structured dataset.

FIG. 2B shows a record 250 of real world data (RWD) for a patient for a timeline. The record 250 is stored in a node 251 configured to store a structured dataset. The data entries 252, 254, 256, and 258 each correspond to a measurement or observation of a common patient associated with the record 250. The patient can be associated with an identifier that identifies the node 251 so that additional entries of the patient record (e.g., for additional measurements in the timeline) are stored in the node 251 and associated with the record 250.

The example record 250 includes four entries 252, 254, 256, and 258, each corresponding to a point in time for the patient treatment. In some implementations, each point in time corresponds to when additional data on the patient is acquired (e.g., by an endoscopy or other doctor visit). However, the timeline need not be related to a doctor visit. The timeline can be updated whenever additional data are added for the patient that correspond to a new time in the timeline (e.g., if the patient completes a survey indicating a status of his symptoms for a particular point in time). Any of the data of data store 201 can be included in the node 251.

The node 251 of the data store can include a physical, hardware memory location in the data store. The nodes (e.g., node 251) can be connected to structure the data store to respond to the structured queries. For high scale data processing, the structure of the data store reduces a latency of query response. The structure of the data store can be based on types of the features detected, a type of disease represented, and/or patient identifier information. The patient identifier information can be a non-personally identifying information (PII) index, such that the data are anonymized. In some implementations, the structure is based on alignment of the features in the video data to the portions of the video data. This enables quick access to relevant portions of the video data in the data store. For example, for tracking disease development over time, different videos for a patient can be aligned to one another based on detected boundaries in the GI tract for the respective endoscopies.

In some implementations, the anatomical location data includes a label indicating an anomaly in the GI tract and a timestamp for video data of the endoscopic data, the timestamp specifying a portion of the video data that represents the anomaly of the GI tract.

In the example record 250, the first entry 252 corresponding to an initial point in time T1 includes endoscopy data (e.g., video data). The video data has two features, each corresponding to a respective tracked symptom 260, 264. Here, the data refers to a state 260*a*, 264*a* of each symptom at the initial time T1. In some implementations, these features are combined into a single instance of data in the entry 252. A procedure report 262*a* is included to detail what endoscopy was performed at T1 (e.g., what location, how long the procedure was, what tools were used, and other relevant data).

A second entry 254 corresponds to a second time point T2 in the timeline. The second entry can be created at any point in time T2 after the initial point in time T1. This can be days, weeks, months, or years later, for example. The entry 254 includes updates for each of the first and second symptoms identified at T1. For example, video data 260*b* corresponds to symptom 1 (e.g., inflammation at location 1) of data 260*a* of T1. Additionally, video data 264*b* of symptom 2 (e.g., inflammation at location 2) corresponds to data 264*a* of T1. A new procedure report 262*b* is generated for the second observation data of entry 254. Additionally, treatment data 266*a* is included specifying what treatment occurred from T1 to T2. This treatment data 266*a* can be related to outcomes at T2, and used to predict future outputs at point T3 and or recommend new treatment.

A third entry 256 corresponds to a third time point T3 in the timeline. The third entry can be created at any point in time T3 after the second point in time T2. The entry 256 includes updates for each of the first and second symptoms identified at T1 and T2, and any new symptoms if applicable. For example, video data 260*c* corresponds to symptom 1 (e.g., inflammation at location 1) of data 260*a* of T1 and 260*b* of T2. Additionally, video data 264*c* of symptom 2 (e.g., inflammation at location 2) corresponds to data 264*a* of T1 and 264*b* of T2. A new procedure report 262*c* is generated for the second observation data of entry 256. Additionally, treatment data 266*b* is included specifying what treatment occurred from T2 to T3. This treatment data 266*a* can be related to outcomes at T3, and used to predict future outputs at point T4 and/or recommend new treatment if the first treatment was ineffective or effective enough to require lower drug dosages, for example.

A fourth entry 258 corresponds to a fourth time point T4 in the timeline. The fourth entry 258 can be created at any point in time T4 after the third point in time T3. The fourth entry 258 includes updates for each of the first and second symptoms identified at T1, T2, and T3, and any new symptoms if applicable. For example, video data 260*c* corresponds to symptom 1 (e.g., inflammation at location 1) of data 260*a* of T1, 260*b* of T2, and 260*c* of T3. Symptom 2 (e.g., inflammation at location 2) has disappeared, so there is no longer data corresponding to data 264*a* of T1, 264*b* of T2, and 264*c* of T3. A new procedure report 262*c* is generated for the second observation data of entry 256. Additionally, treatment data 266*c* is included specifying what treatment occurred from T3 to T4. This treatment data 266*a* can be related to outcomes at T4, and used to predict future outputs as previously described.

As subsequently described, a machine learning model can be associated with each corresponding data source over the timeline, such as video data 260 for symptom 1, video data 264 for symptom 2, procedure data 262, and treatment data 266. In some implementations, the video data 260, 264 for multiple symptoms can be analyzed in a common machine learning model. Each of these machine learning models is combined into a global model for generation of final predictions to relate each of the sources 260, 262, 264, and 266 of the timeline of record 250.

As subsequently described, each entry 252, 254, 256, and 258 can be associated with the colon disease severity score indicating the severity of the disease at the respective point in time T1, T2, T3, and T4. This scoring data are included in the record 250 for use in predicting future disease severity (e.g., using at least one of the scores, but typically two or more of the scores).

Figure 3:
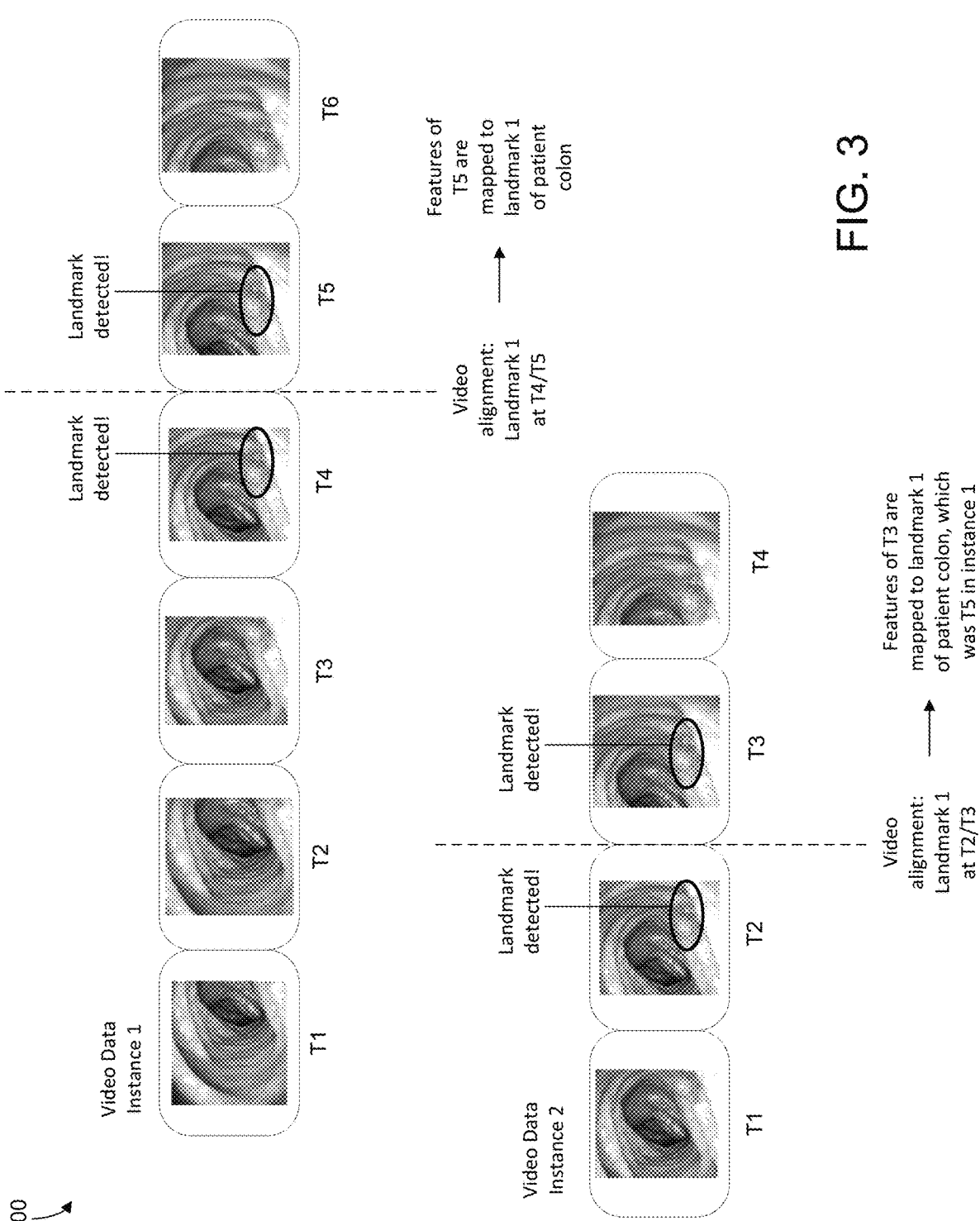
FIG. 3 shows examples of segmenting video data.

FIG. 3 shows an example diagram 300 of longitudinal alignment of colon videos over multiple time instances is performed (e.g., by the data processing system 100 of FIG. 1.). A video recorded of a full colonoscopy from insertion, (an initial time), to full withdrawal, time (an end time). These videos can be screening videos for colorectal cancer detection (CRC) or Irritable Bowel disease (IBD) videos to assess/monitor Ulcerative colitis (UC) or Crohn's diseases (CD) video. These videos will record the entire procedure, insertion of the scope will reach the cecum (CRC, UC) and may proceed to the ileum (UC, CD) and may end with a retoflexion to rectum prior to removal of the scope.

Coarse alignment of video of the same patient over time is performed. Insertion and withdrawal time is variable depending of the physician and findings and the length of the colon is variable depending of each patient. In order to align a recording, the algorithm will first detect boundary landmark and record the time code (TC). These landmarks are: Cecum detected by recognizing the cecal valve, the appendix orifice or the crow path pattern of the colon; Ileum by detecting its particular colon wall pattern; a transverse colon detected by it characteristic triangular pattern. These are non-disease features.

Given the sequential nature of the video the various time stamps allows the data processing system a recognize which section is represented in the video data currently and allow the data processing system to align these landmarks over the various time points, shown in FIG. 3.

An example chronology of colon features includes the following: an Ileum; a cecum (e.g., alignment landmark is TC_cecum); an ascending colon; an end of the ascending colon and beginning of a transverse colon (e.g., alignment landmark is TC_beg_trans); an end of the transverse colon and beginning of descending colon (e.g., alignment landmark is TC_end_trans); and a rectum (e.g., align landmark is Tc_rectum). At this step the various colon section are anatomically align and time codes are matched A medium alignment of the video data for the same patient is performed. Once the segments/sections are aligned, further time based alignment can be performed for further accuracy. An optical flow algorithm can used to detect hovering in a particular spot of the colon, or an image correlation algorithm can be used to detect quasi-stationary motion of the scope. For a given section, the travel time (TT) in the colon is given by: TT=TC_end_section−TC_beg_section−stationary time. A first approximation is performed in which the velocity is constant, so a given motion speed in unit of frames (SpFrame) is given by SpFrame=TT/(number of frame in colon section). Given the SpFrame for a section for 2 videos we can further rfine the location of image within a section of the colon.

A fine colon alignment of the video data is performed. Once the approximate location In a given section of the colon is defined, colon features such as hostra can be matched by normalized image, correlation or any known pattern matching techniques, to precisely match specific segments of the colon across different videos.

The data processing system performs feature mapping of the colon. A state of a colon disease such as UC or CD is typically graded using a numerical scale such as the eMS mayo score for UC or SES-CD score for Crohn's disease. The determination of the score depends on specific feature on the colon wall and there is no one-to-one correspondence between scores and underlined featured.

Once longitudinal alignment is achieved and a fine grain score is computed by the data processing system, evolution of the disease can be tracked along the colon from time point to time point. A notable enhancement is to characterize a given location or segment of the colon not by the score but by disease burden, such as by characteristics of the underline features that led to a given score. Typical features include (as previously described): ulceration, erosion, erythema, a reduced vascularization or a loss of vascularization, and friability. The features can be tracked over time and several important characteristics can be computed such as a size of the feature, a density of the feature, or an extent of feature presence. These features can be mapped to the corresponding subsection of the colon and their evolution and attributes tracked over time to assess disease progression, and remission.

Phenotipical characterization of a section of colon is performed by the data processing system. Generally, each of these individual features found along with a given attribute constitutes a separate a feature. In order to reduce dimensionality of the overall feature vector, various section of colon can be grouped together. A typical dimensional grouping of feature can include: by anatomical sections of the colon (e.g., ileum, cecum, ascending, transverse, descending, rectum, etc.); by "alike feature" where frames are sequentially grouped by inventorying the major feature in a frame and extending to sequential frames with the same major feature; and by arbitrarily dividing the color in time based segments. Once an aggregation is defined, and notable characteristics of the feature is decided an endoscopic feature vector is formed and represent a phenotype for the colon. For example such a vector can include ileum average size of erosion, ileum extent of erosions, ascending colon average ulceration size, ascending colon erosion density, a transverse colon average ulceration size, transverse colon erosion density, descending colon average ulceration size, and descending colon erosion density.

In order to facilitate analytical analysis of the phenotype, each entry is normalized in a consistent way. For example, each normalized feature is between 0 and 1 and the feature vector plot can easily be visualized in a radar or spider plot where each spoke is a normalized feature and you can compare evolution over time for a given patient, or patient of a cohort for a given time point. The endoscopic feature vector can be extended to include non-video based data to represent a more extensive phenotype, as described herein. These can include histologic data, PROC data biomarkers, and omics data.

The longitudinal alignment of colon videos described in relation to diagram 300 can facilitate clustering of patient data, described below. For example, the alignment of the video data enables common features to be analyzed over time for a patient. Additionally, alignment of the video data and landmark detection each facilitate clustering of patients by comparing video data representing common portions of the GI tract across different patient populations.

Figure 4:
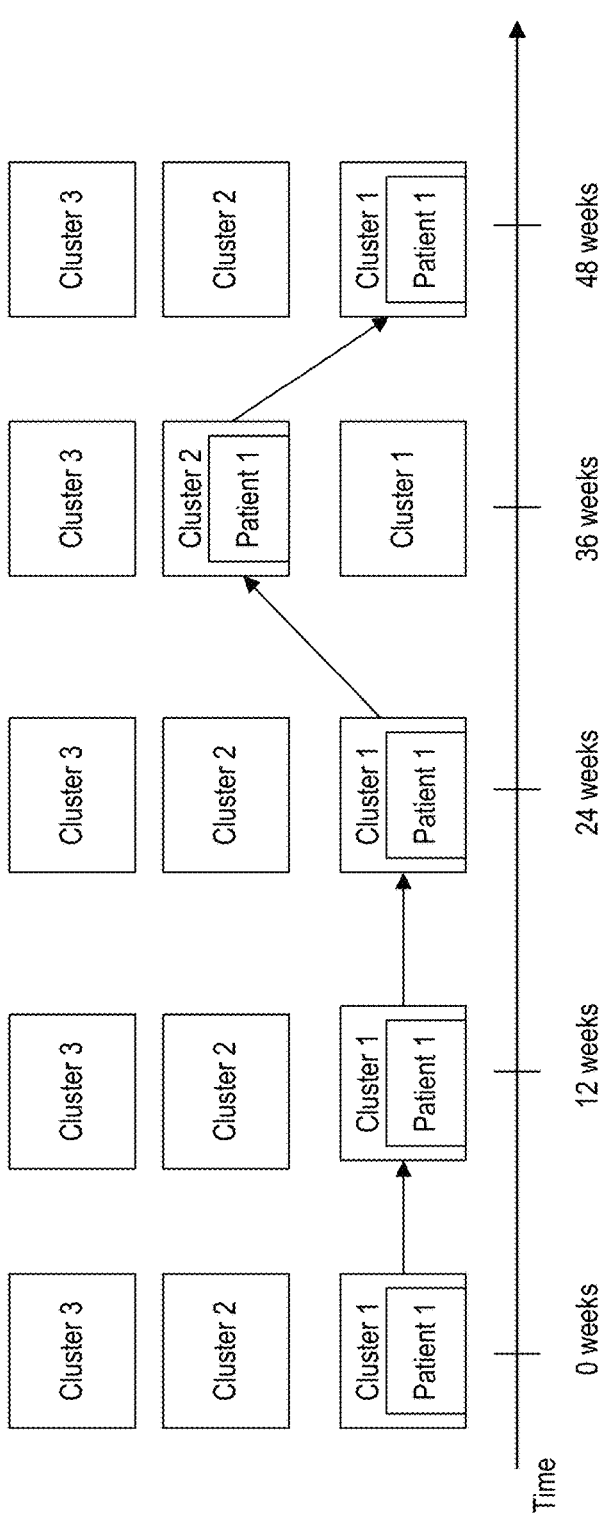
FIG. 4 shows an example of a timeline of clusters.

FIG. 4 shows dynamic clustering of data in diagram 400. Once the notion of feature vector or equivalently phenotype is established, you can group the various patients in clusters of consistent characteristic. A typical method to use for clustering are K-mean, modified K-mean, Bayesian analysis or mixed model analysis. In order to facilitate interpretation of the results and understand interaction between these features, it is customary to look at clustering along 2 or 3 distinct features at a time. The data processing system can use principal component analysis to look at the first 2 or 3 top component to achieve clustering. Once a base cluster is establish at time 0, you can follow the cluster over time and re-cluster. Some patient will change clusters but more typically some cluster will split in sub cluster that will follow their own trajectory over time. In a pharma trial, likely clusters are control vs medicated patients and sub cluster emerge during the induction phase as drug affect various patients differently.

The timeline shows entries at 0 weeks (e.g., a first instance of an endoscopy), at 12 weeks (e.g., 12 weeks after the first endoscopy), 24 weeks, 36 weeks, and 48 weeks. A patient (patient 1) is associated with one of 3 clusters: cluster 1, cluster 2, or cluster 3. Each cluster includes features that are considered a common phenotype. In some implementations, each cluster represents patients having similar disease progression. For example, patients in a cluster can have similar average ulcer size and counts, show similar stricturing, and so forth.

A patient's progression in various clusters is tracked over time. For example, patient 1 is part of cluster 1 for the first 24 weeks. However, at 36 weeks, patient 1 has symptoms that diverge from cluster 1. This may be evidence of increased severity of the patient's disease. In this case, the patient can receive a change in treatment, relative to other patients of the cluster. The patient, once treated, again joins cluster 1. This can represent a lessening of severity for the symptoms of patient 1, indicating successful treatment.

A processes for training and developing machine learning models for prediction of each of colon disease severity and treatment outcomes (e.g., by machine learning module 113 of FIG. 1) are now described. The process includes receiving video data 102, EMR data 204, registry data 208, and omics data 206. While these data 102, 204, 206, and 208 are specifically discussed, other data (as previously described) can be incorporated into the machine learning model. The machine learning module 113 is configured to perform video truncation to extract video data for processing. Truncation can include removing portions of the video data that are not relevant to the scoring process because the portions do not include relevant data, include redundant data, or include data that is noisy or otherwise unusable (e.g., image frames that are out of focus, not illuminated, and so forth). This process can be used for longitudinal alignment as well.

The machine learning module 113 is configured to de-identify the video data. This can include data masking, anonymization, data scrambling, removal of portions of the data, and so forth. In some implementations, the de-identification of the video data can be performed by another module or system besides the machine learning model 113. For example, the de-identification of the data can be performed by an interfacing module before any data are processed by the machine learning model 113. In another example, the de-identification of the data can be performed prior to storage of the data 102, so that data accessed the data processing system are already anonymized.

The machine learning module 113 is configured to perform video cataloging. This includes structuring the video data 102 based on metadata associated with the video data. The metadata may be generated when the video data are generated, or can be associated with the video data during cataloging. The metadata may include identifications of an operation associated with the video data 102, a timestamp, and so forth.

The machine learning module 113 is configured to perform annotation of the video data 102. The annotation is based on image processing of the video. Annotations can be associated with each video frame, or with portions of the video clip. This can provide both frame-level data, which includes annotations associated with individual frames of the video data 102. Frame level annotations can include data relevant to a particular frame. For example, the frame level annotations may include data represented whether bleeding is observed, a number of polyps, in the image, and/or a location in the tract associated with the particular image frame. The annotations are also case level annotations, which include annotations describing entire videos including multiple image frames. The case level annotations include information about the video overall, such as aggregates of annotations stored with individual frames. This can include annotations indicating that, for example, bleeding was observed a particular number of times in the video, or not at all. In another example, a total number of polyps that were observed can be included in the case level annotations. In another example, a percentage of frames including polyps, bleeding, neither, or both can be included in the annotations. Other such annotations can be included at the case level.

In some implementations, the machine learning module 113 is configured for data de-identification. After de-identification, the machine learning module 113 is further developed based on receiving data from the additional sources 103, such as EMR data 104, registry data 208, and omics data 206. The machine learning module 113 obtains clinical informatics for each of these data sources. This can include structuring the data (e.g., in the database 251 of FIG. 2B). In some implementations, the informatics are obtained by identifying an existing structure for the data 204, 206, and 208. In some implementations, the process 300 includes feature extraction from these data by the machine learning module 113. These data 104, 106, 108 are also de-identified for use in the machine learning model. These data can also be stored as real world data (RWD) in a database. This database can be used for one or more downstream applications. In some implementations, the data are not de-identified for processing.

In some implementations, a machine learning model includes a convolutional neural network (CNN). A convolutional neural network (CNN) can be configured based on a presumption that inputs to the neural network correspond to image pixel data for an image or other data that includes features at multiple spatial locations. For example, sets of inputs can form a multi-dimensional data structure, such as a tensor, that represent color features of an example digital image (e.g., an image of the surroundings of a vehicle). In some implementations, inputs to the neural network correspond to a variety of other types of data, such as data obtained from different devices and sensors of a vehicle, point cloud data, audio data that includes certain features or raw audio at each of multiple time steps, or various types of one-dimensional or multiple dimensional data. A convolutional layer of the convolutional neural network can process the inputs to transform features of the image that are represented by inputs of the data structure. For example, the inputs are processed by performing dot product operations using input data along a given dimension of the data structure and a set of parameters for the convolutional layer. In some implementations, the model includes other types of digital neural networks, such as a recurrent neural network (RNN), a radial basis function network, a deconvolution network, a variational auto-encoder (VAE), generative adversarial network (GAN) and so forth.

FIG. 5 shows a flow diagram showing a process for processing video data representing colonoscopies of a patient to track an evolution of a disease in the colon of a patient over time, based on data sources 202, 204, 206, and 208 and scoring data 501 performed from scoring colon disease severity (or other disease severity). Generally, once the standardized and/or normalized data of each of the sources 202, 204, 206, 208, and 501 are received, the data processing system 100 selects some or all of the data (e.g., data 103 and scoring data 501) from a plurality of time points (e.g., generally three or more time points). The data from each of the time points correspond to observations or measurements for a particular patient at a particular region or location (or for a particular symptom). The observations or measurements are associated with one another in the RWS data store 201, such as with in index or other structured data set. For example, each patient can be represented by a node in structured data set. The node stores an index value representing the patient. The node stores data for each observation or measurement for the patient for each location, symptom, etc. of the patient. Each tracked symptom or disease is correlated to other measurements or observations for that patient in a respective patient timeline. In this way, the progression of disease symptoms is tracked for the patient. When the data are sent to the machine learning model(s), each instance representing the observation or measurement on the timeline corresponds to a feature input into the respective model.

The process 500 includes obtaining (502) video or image data from endoscope (e.g., colonoscopy). The process 500 includes segmenting (504) the video data into segments representing portions of a colon of the patient. The process 500 includes extracting (506), from the video data based on the segmenting, a set of features representing locations in the colon of the patient. The process 500 includes registering (508) the feature vector as representing the colon of the patient for tracking the evolution of the disease in the colon of the patient.

While this specification includes many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

In some implementations, determining the prediction includes determining one or more frame level annotations corresponding to individual frames of a video of the image data; determining one or more case level annotations for the video of the image data; and determining, based on the one or more frame level annotations and the one or more case level annotations, the score associated with the video of the image data.

In some implementations, the one or more features comprise values representing at least one of: a presence of ulcers in the GI tract, a number of ulcers in the GI tract, a relative vascularity of the GI tract, a presence of erosions in the GI tract, a number of the erosions in the GI tract, a presence or absence of bleeding in the GI tract, a number of times bleeding is observed in the GI tract, a friability in the GI tract, a size of ulcers or erosions in the GI tract, a presence of stenosis in the GI tract, a total ulcerated surface in the GI tract, a presence of cobblestoning in the GI tract, a type of Crohn's disease observed, a presence of dysplasia in the GI tract, and whether activity at a biopsy site is proximal or distal; and wherein the prediction representing a severity of colon disease in the patient is based on the values of the one or more features.

In some implementations, process includes receiving electronic medical records (EMR) data for the patient, the EMR data including medical information about the patient, wherein the machine learning model is trained with labeled EMR data associating values of medical information of patients with respective severity of colon disease in the patients; extracting one or more values from the EMR data to form an EMR feature vector; processing, by the machine learning model or by a second machine learning model in addition to the machine learning model, the EMR feature vector.

In some implementations, the one or more features of the EMR feature vector comprise values representing at least one of: an age of the patient, a sex of the patient, a reproductive history of the patient, a smoking status of the patient, a race or ethnicity of the patient, a presence or absence of an anal fissure in the patient, a fistula or abscess in the patient, and the presence or absence of one or more complications such as uveitis, pyoderma gangernosum, erythema nodosum, and/or arthralgia in the patient, serological profiling results of the patient, a history of medications prescribed to the patient, a history of surgery for the patient, a degree of induration for the patient, a presence or size of an abdominal mass in the patient, a history of flaring in the patient, a hospitalization history for the patient, and a history of thrombosis for the patient.

In some implementations, the process includes receiving registry data for the patient, the registry data including patient data across patient populations, wherein the machine learning model is trained with labeled registry data associating values of for patient populations with respective severity of colon disease in particular patients of the patient populations; extracting one or more values from the registry data to form a registry feature vector; processing, by the machine learning model or by a second machine learning model in addition to the machine learning model, the registry feature vector; and generating an updated prediction representing the severity of colon disease in the patient indicated by the registry data or a or treatment recommendation for the patient. In some implementations, the one or more features of the registry feature vector comprise values representing at least one of: results and other data from studies, experiments, and clinical trials that test treatment regimens that are associated with the patient including one or more of drug therapy, physical therapy, or surgery, specific diagnoses associated with the patient, procedures, and application of drugs associated with the patient.

In some implementations, the process includes receiving omics data for the patient, the omics data including genetic or molecular profiles of patient populations, wherein the machine learning model is trained with labeled omics data associating values of genetic or molecular profiles with respective severity of colon disease in the patients of the patient populations; extracting one or more values from the omics data to form an omics feature vector; processing, by the machine learning model or by a second machine learning model in addition to the machine learning model, the omics feature vector; and generating an updated prediction for the severity of colon disease in the patient indicated by the omics data or a treatment recommendation for the patient.

In some implementations, the one or more features of the omics feature vector comprise values representing at least one of: transcriptomics data such as sets of RNA molecules, including mRNA, rRNA, tRNA, and other non-coding RNAs relevant to treatment outcomes; one or more phenotypic traits of the patient; microbiome data for the patient; genome sequencing for the patient; bisulfite sequencing (RRBS) data of the patient; ChIP-sequencing for the patient; HLA-DR genotyping for the patient; a 16s microbiome sequence from stool of the patient; a 16s microbiome sequence from a biopsy of the patient; epithelial cell profiling from biopsy of the patient; a single cell assay from a biopsy of the patient; a single-cell RNA sequence from a biopsy of the patient; fecal calprotectin or lactoferrin of the patient; Haematocrit levels for the patient; serum CRP/C-reactive protein levels in the patient; Pharmacokinetics (PK) data associated with a patient; white blood cell counts (WBC), hemoglobin (HgB), platelets, albumin, creatinine, and/or ESR levels of the patient; a urea analysis of the patient; liver function tests of the patient; ferritin, B12, Folate and/or VitD levels in the patient; SCFA levels in stool of the patient; and basal metabolite panel in the patient.

In some implementations, the machine learning model comprises a convolutional neural network (CNN) or other models, and wherein the each of the instances of symptoms of colon disease contributes to an activation value for inputting into a layer of the CNN.

In some implementations, processing the feature vector comprises performing a classification with detection bounding boxes and segmentation pixel-wise masks on the image data.

In some implementations, generating the machine learning model includes receiving image data including ground truth scores; labeling the image data; performing frame sampling and score assignment to the frames; applying training data to the machine learning model at a frame level and at a case level; optimizing the machine learning model with validation data at the frame level and the case level; applying test data that is not annotated; and performing case level evaluation of the test data.

Figure 6:
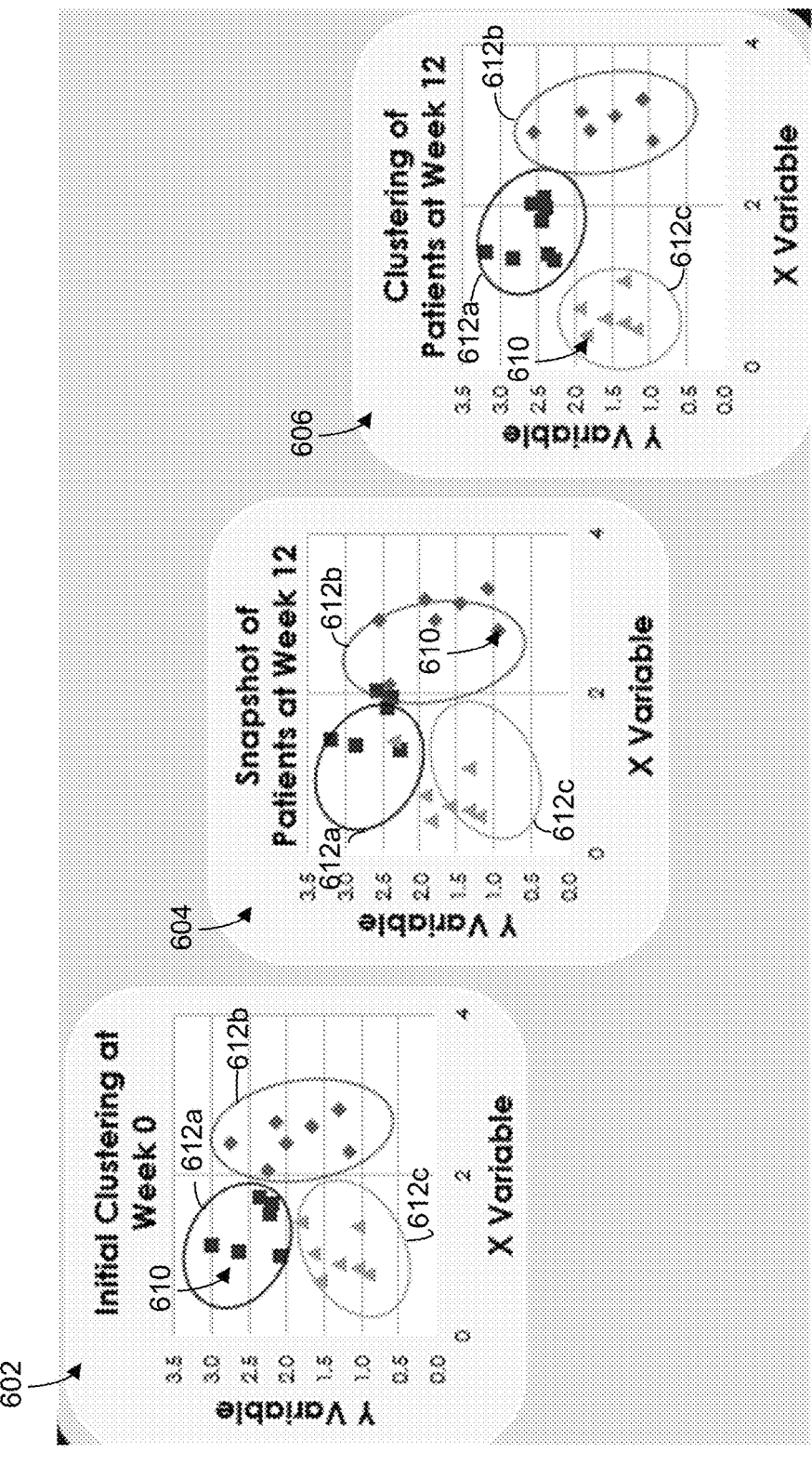
FIGS. 6-7 show example output data.

FIG. 6 shows example output data 600 including patient clusters. At graph 602, an initial set of three clusters is shown. Patients, represented by data points 610 within the graph, are clustered into clusters 612a, 612b, and 612c. The clusters 612a-c group patients associated with feature sets that are above a threshold similarity to feature sets for other patients in the group. In graph 604, the patient data of 12 weeks are analyzed as previously described. The data points 610 move slightly to represent the updated feature sets associated with each of the patients. The clusters 612a-c are recalculated, as shown in graph 606. The patients are then associated with their updated clusters.

Figure 7:
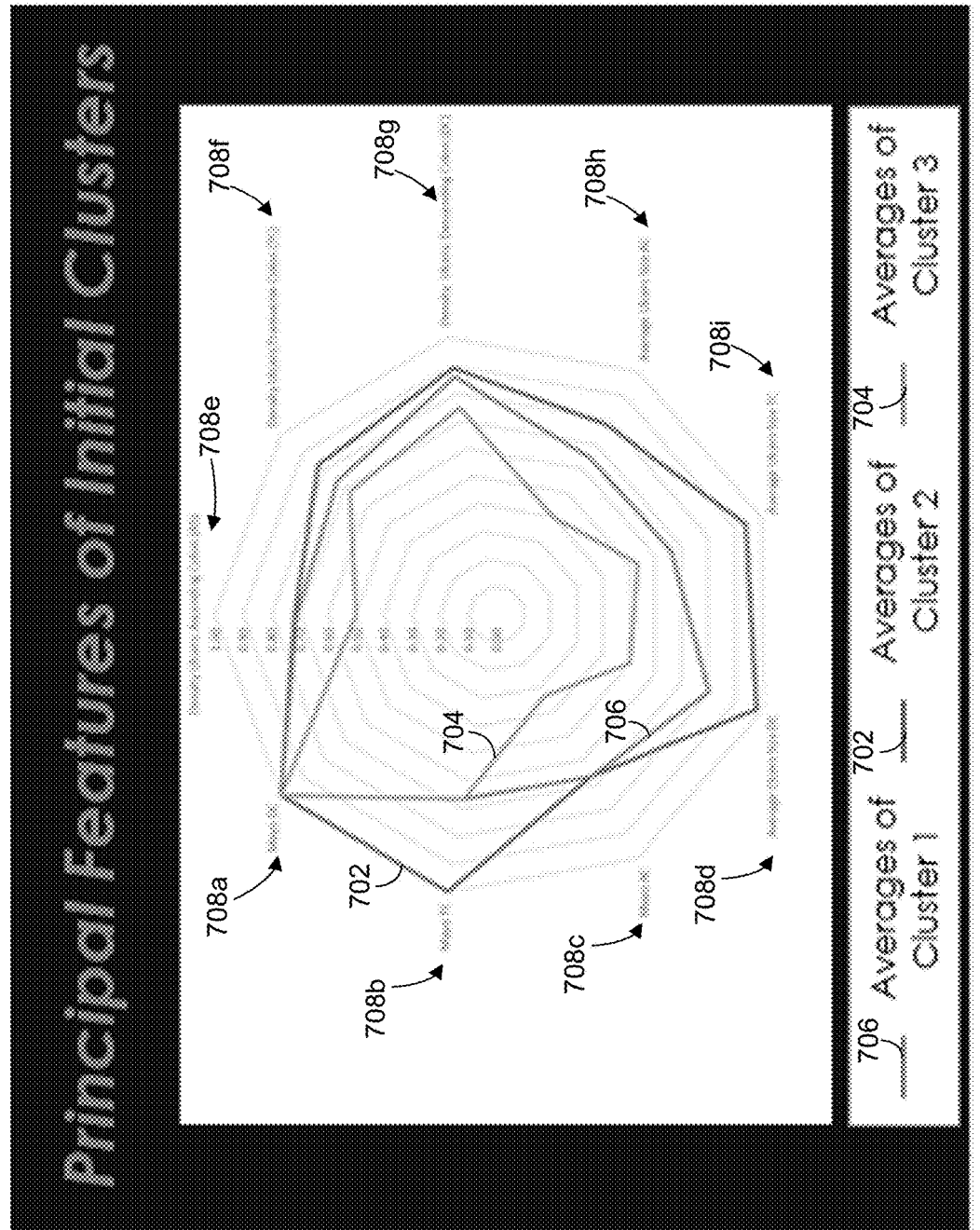

FIG. 7 shows a graph 700 representing clusters for patients. The clusters are shown as average feature set values of features 708a-i. Three clusters are defined: cluster 1 including average feature 708 values shown by line 706, cluster 2 including average feature 708 values shown by line 702, and cluster 3 including average feature 708 values shown by line 702. Graph 700 shows a representation of how the clusters are being defined by the values of their included feature sets. Here, the feature sets including features 708a-i are common across all three clusters.

FIG. 8 shows a flow diagram representing a process 800 for tracking disease progression in patients. Process 800 includes a method for tracking an evolution of a disease in a colon of a patient over time. The process 800 includes obtaining (802) video data representing a colon of a patient. The process 800 includes segmenting (804) the video data into segments representing portions of the colon. The process 800 includes detecting (806) one or more features of the colon for each segment of the segments. The process 800 includes generating (808), from the one or more features of the colon, a feature vector representing the colon of the patient. The process 800 includes generating (810) a timeline that tracks the evolution of the disease in the colon of the patient based on the feature vector. In some implementations, the timeline includes entries representing different points in time for the evolution of the disease for the patient, and wherein each entry of the timeline is based on a feature vector generated at the point in time for that entry. In some implementations, the process 800 further includes predicting a disease progression of the disease at a future point in time based on one or more existing entries in the timeline. In some implementations, the process 800 incudes predicting a disease progression of the disease at 52 weeks from an initial time based on a first feature vector representing the patient at the initial time and based on a second feature vector representing the patient at twelve weeks from the initial time.

FIG. 9 shows a flow diagram representing a process 900 for tracking disease progression in patients. Process 900 includes a method for tracking an evolution of a disease in a colon of a patient over time. The process 900 includes obtaining (902) video data representing a colon of a patient. The process 900 includes segmenting (904) the video data into segments representing portions of the colon. The process 900 includes detecting (906) one or more features of the colon for each segment of the segments. The process 900 includes generating (908), from the one or more features of the colon, a feature vector representing the colon of the patient. The process 900 includes generating (910) a cluster comprising the feature vector, the cluster representing a type of colon disease and a given point in time of an evolution of the colon disease.

In some implementations, a data processing system performs processes 800 and/or 900 for processing video data representing colonoscopies of a patient to track an evolution of a disease in the colon of a patient over time. The data processing system includes an interface configured to receive video data from a camera, the video data representing a colonoscopy for a patient. The data processing system includes at least one processor configured to perform additional operations comprising: obtaining the video data via the interface; determining a type of disease screening associated with the video data; performing coarse alignment of the video data over a time period based on the type of disease screening, the coarse alignment comprising: segmenting the video data into segments representing portions of a colon of the patient; and assigning a time period to each segment. The operations include performing a medium alignment of the video data based on the coarse alignment, the medium alignment comprising: determining a motion of the camera through a portion of the colon represented by a segment; and determining a location of the camera within the segment for a given time in the time period of the segment. The operations include performing a fine alignment of the video data based on the medium alignment, the fine alignment comprising: associating one or more features of the colon detected in the segment with a feature time stamp; generating, from the one or more features of the colon detected based on the fine alignment, a feature vector representing the colon of the patient; and generating a timeline comprising the feature vector and one or more other feature vectors representing the patient at respective points in the timeline, the timeline representing an evolution of a colon disease over time in the patient. In some implementations, the data processing system includes a user interface configured to present output data representing the timeline.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

What is claimed is:

1. A method for tracking an evolution of a disease in a colon of a patient over time, the method comprising:
   receiving video data representing a colon of a patient;
   segmenting the video data into segments representing portions of a colon of the patient;

extracting, from the video data based on the segmenting, a set of features representing locations in the colon of the patient, the set of features forming a feature vector; and
   registering the feature vector as representing the colon of the patient for tracking the evolution of the disease in the colon of the patient.

2. The method of claim 1, further comprising:
   generating a timeline representing the evolution of the disease in the patient, the timeline configured to associate each feature vector registered as representing the colon of the patient; and
   generating a plurality of feature vectors that are registered to the colon of the patient, each feature vector representing the colon of the patient at a different point in time on the timeline.

3. The method of claim 1, further comprising: clustering the feature vector with one or more other feature vectors registered to respective other colons of other patients, wherein clustering comprises:
   comparing first values of the features of the feature vector to second values of features of the one or more other feature vectors; and
   grouping the feature vector and another feature vector when the first values and the second values are within a threshold similarity.

4. The method of claim 1, further comprising:
   obtaining non-video data comprising at least one of histology data for the patient, bio-markers data for the patient, and omics data of the patient; and
   extracting one or more additional features from the non-video data for adding to the feature vector.

5. The method of claim 1, further comprising:
   generating a second feature vector for a second patient based on second video data representing the second patient; and
   registering the second feature vector as representing a colon of the second patient for tracking the evolution of the disease in the colon of the second patient, the second feature vector being stored in a registry with the feature vector for a same time point in a timeline.

6. The method of claim 1, wherein a feature in the set of features represents at least one of a detected ulceration, a detected erosion, a detected erythema, a detected reduced vascularization, tumors, polyps, or a detected friability.

7. The method of claim 1, wherein a feature of the set of features is associated with additional data specifying one or more of a size of the feature, a density of the feature in the colon, and an extent of the feature in the colon.

8. The method of claim 1, further comprising performing dimensional grouping of features of the set of features based on at least one of:
   an anatomical section of the colon or segment of the video data;
   a frame sequence including the features; and
   a time value associated with one or more of the features.

9. The method of claim 1, further comprising labeling the feature vector based on the features of the feature vector, the label specifying at least one of an ileum average size of erosion, an ileum extent of erosions, an ascending colon average ulceration size, an ascending colon erosion density, a transverse colon average ulceration size, a transverse colon erosion density, a descending colon average ulceration size, and a descending colon erosion density.

10. The method of claim 1, wherein the video data represent a scope of the colon of the patient including at least one of a cecum, an ileum, and a rectum of the patient.

11. The method of claim 1, further comprising:
    extracting a set of features from the video data based on a type of disease screening associated with the video data, wherein the set of features for the video are unique to the type of screening.

12. The method of claim 11, wherein the type of disease screening comprises at least one of cancer detection, irritable bowel disease, ulcerative colitis, and Crohn's disease.

13. The method of claim 1, further comprising generating one or more clusters including the feature vector, wherein each cluster is associated with a particular set of variables that define a phenotype associated with that cluster.

14. The method of claim 13, wherein the cluster is associated with output data, the output data being output with the cluster, the output data comprising at least one of:
    a number of patients in the cluster for a specified time period;
    an average value for each variable in the cluster; or
    a range of values for each variable in the cluster.

15. A method for tracking an evolution of a disease in a colon of a patient over time, the method comprising:
    obtaining video data representing a colon of a patient;
    segmenting the video data into segments representing portions of the colon;
    detecting one or more features of the colon for each segment of the segments;
    generating, from the one or more features of the colon, a feature vector representing the colon of the patient; and
    generating a timeline that tracks the evolution of the disease in the colon of the patient based on the feature vector.

16. The method of claim 15, wherein the timeline includes entries representing different points in time for the evolution of the disease for the patient, and wherein each entry of the timeline is based on a feature vector generated at the point in time for that entry.

17. The method of claim 16, further comprising predicting a disease progression of the disease at a future point in time based on one or more existing entries in the timeline.

18. The method of claim 17, further comprising predicting a disease progression of the disease at 52 weeks from an initial time based on a first feature vector representing the patient at the initial time and based on a second feature vector representing the patient at twelve weeks from the initial time.

19. The method of claim 17, further comprising:
    generating a cluster comprising the feature vector, the cluster representing a type of colon disease and a given point in time of an evolution of the colon disease.

20. A data processing system for processing video data representing colonoscopies of a patient to track an evolution of a disease in a colon of a patient over time, the data processing system comprising:
    an interface configured to receive video data from a camera, the video data representing a colonoscopy for a patient;
    at least one processor configured to perform operations comprising:
    obtaining the video data via the interface;
    determining a type of disease screening associated with the video data;
    performing coarse alignment of the video data over a time period based on the type of disease screening, the coarse alignment comprising:
    segmenting the video data into segments representing portions of a colon of the patient; and
    assigning a time period to each segment;
    performing a medium alignment of the video data based on the coarse alignment, the medium alignment comprising:
    determining a motion of the camera through a portion of the colon represented by a segment; and
    determining a location of the camera within the segment for a given time in the time period of the segment;
    performing a fine alignment of the video data based on the medium alignment, the fine alignment comprising:
    associating one or more features of the colon detected in the segment with a feature time stamp;
    generating, from the one or more features of the colon detected based on the fine alignment, a feature vector representing the colon of the patient; and
    generating a timeline comprising the feature vector and one or more other feature vectors representing the patient at respective points in the timeline, the timeline representing an evolution of a colon disease over time in the patient; and
    a user interface configured to present output data representing the timeline.

* * * * *